United States Patent
Wong Po Foo et al.

(10) Patent No.: US 9,011,914 B2
(45) Date of Patent: Apr. 21, 2015

(54) HETERO-ASSEMBLED HYDROGELS

(75) Inventors: Cheryl Wong Po Foo, Palo Alto, CA (US); Sarah C Heilshorn, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 987 days.

(21) Appl. No.: 12/455,996

(22) Filed: Jun. 9, 2009

(65) Prior Publication Data
US 2010/0183720 A1    Jul. 22, 2010

Related U.S. Application Data

(60) Provisional application No. 61/060,144, filed on Jun. 10, 2008.

(51) Int. Cl.
*A61K 47/42*    (2006.01)
*A61K 9/00*    (2006.01)

(52) U.S. Cl.
CPC .............. *A61K 9/0024* (2013.01); *A61K 47/42* (2013.01)

(58) Field of Classification Search
None
See application file for complete search history.

(56) References Cited

U.S. PATENT DOCUMENTS

| | | | | |
|---|---|---|---|---|
| 6,090,911 | A * | 7/2000 | Petka et al. | 530/300 |
| 6,129,761 | A | 10/2000 | Hubbell | |
| 7,229,634 | B2 | 6/2007 | Tirrell | |
| 7,371,719 | B2 | 5/2008 | Stupp | |
| 2004/0242469 | A1 | 12/2004 | Lee | |
| 2007/0099840 | A1 | 5/2007 | Ulijn | |
| 2008/0145934 | A1 | 6/2008 | Harris | |

OTHER PUBLICATIONS

Petka et al., Science, 1998, vol. 281, pp. 389-392.*
Kanelis et al. Nature Structural Biology, 2001, vol. 8, pp. 407-412.*
Ramachandran et al. Biomacromolecules, 2005, 6, 1316-1321.*
Guler et al. (2006). Presentation of RGDS Epitopes on Self-Assembled Nanfibers of Branched Peptide Amphiphiles. Biomacromolecules 2006-7(6):1855-1863.
Schneider et al. (2002) Responsive Hydrogels from the Intramolecular Folding and Self-Assembly of a Designed Peptide. J. Am. Chem. Soc. 2002-124(50):15030-15037.
Petka et al. (1998). Reversible Hydrogels from Self-Assembling Artificial Proteins. Science (1998)-281:389-392.
Shen et al. (2007). Structure and mechanical properties of artificial protein hydrogels assembled through aggregation of leucine zipper peptide domains. Soft Matter 2007-3:99-107.
Shen et al. (2006). Tuning the erosion rate of artificial protein hydrogels through control of network topology. Nature Materials 20065:153-158.
Kanelis et al. (2001). Solution structure of a Nedd4 WW domain-ENaC peptide complex. Nature Structural Biology 2001-8(5):407:412.
Russ et al. (2005). Natural-like function in artificial WW domains. Nature 2005-437:579:583.

* cited by examiner

*Primary Examiner* — Karlheinz R Skowronek
*Assistant Examiner* — Roy Teller
(74) *Attorney, Agent, or Firm* — Lumen Patent Firm

(57) ABSTRACT

A two-component, molecular-recognition gelation strategy that enables cell encapsulation without the need for environmental triggers is provided. The two components, which in one example contain WW and polyproline-rich peptide domains that interact via hydrogen bonds, undergo a sol-gel phase transition upon simple mixing. Hence, physical gelation is induced by the mixing of two components at constant environmental conditions, analogous to the formation of chemically crosslinked epoxies by the mixing of two components. Variations in the molecular-level design of the two components are used to predictably tune the association energy and hydrogel viscoelasticity. These hetero-assembly physical hydrogels encapsulate neural progenitor cells at constant physiological conditions within 10 seconds to create uniform 3D cell suspensions that continue to proliferate, differentiate, and adopt well-spread morphologies.

7 Claims, 14 Drawing Sheets

Protein A

Protein B

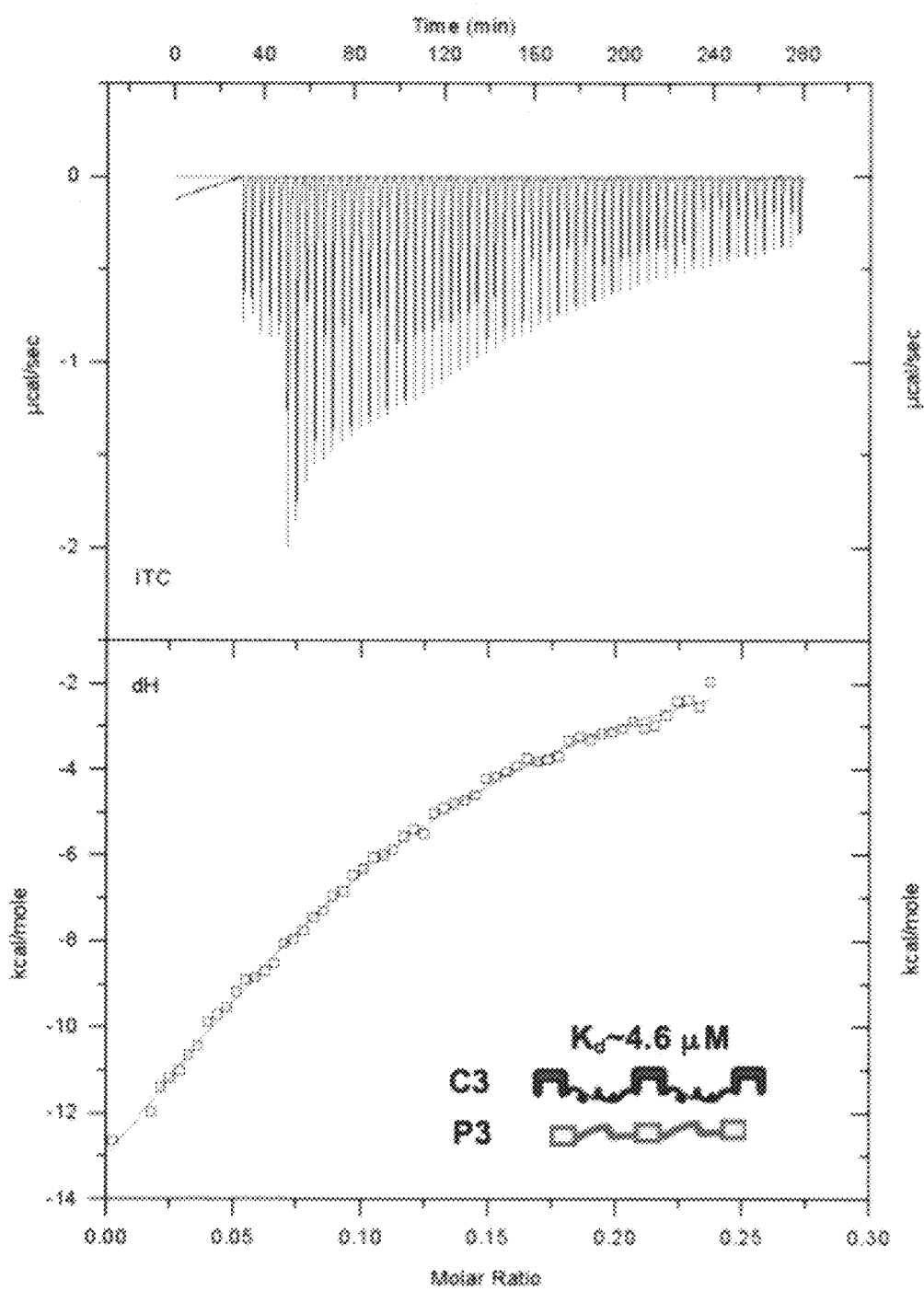

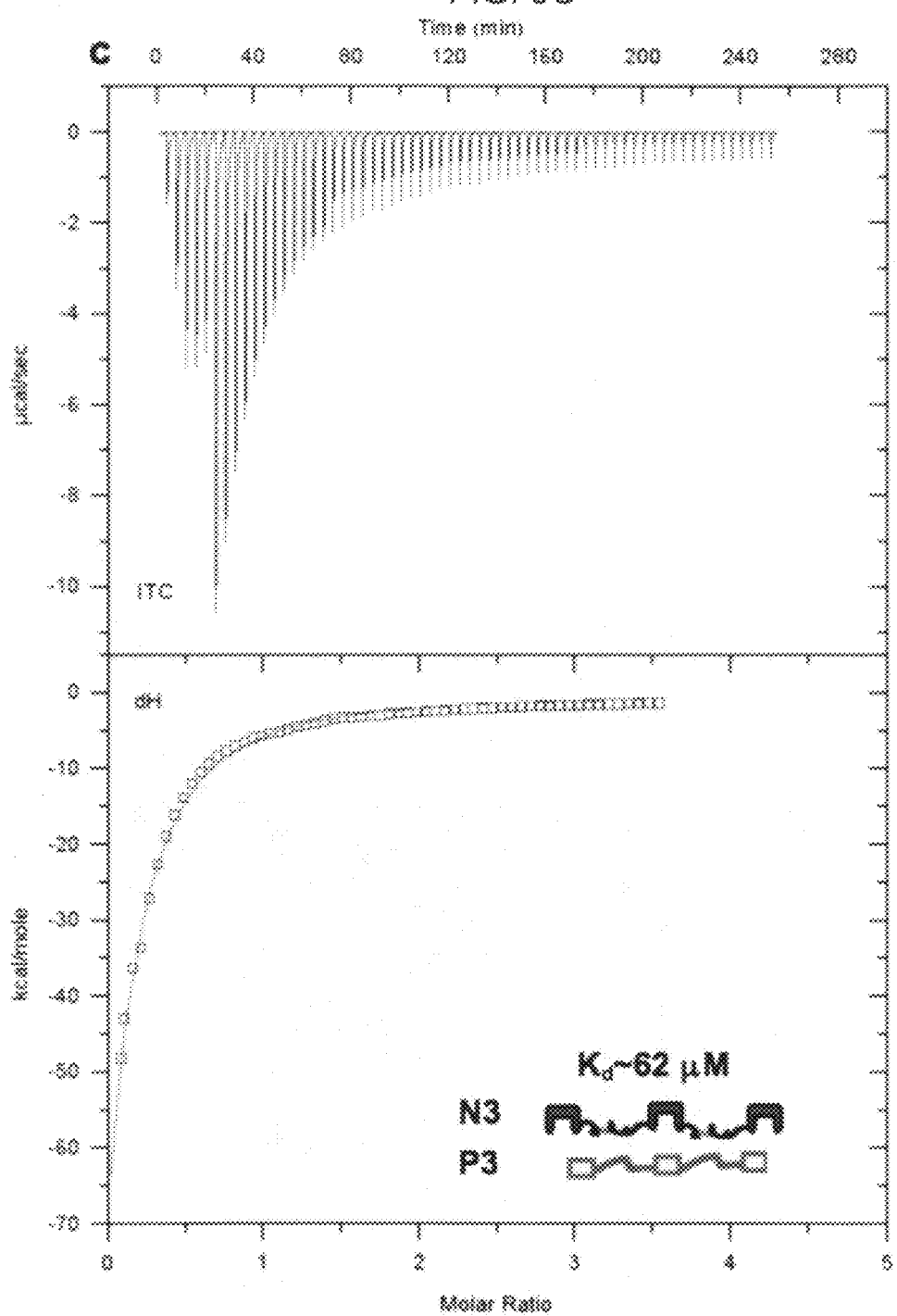

SEQUENCE LISTING

<160> NUMBER OF SEQ ID NOS: 10

<210> SEQ ID NO 1
<211> LENGTH: 34
<212> TYPE: PRT
<213> ORGANISM: Artificial Sequence
<220> FEATURE:
<223> OTHER INFORMATION: Computationally derived
<220> FEATURE:
<221> NAME/KEY: MISC_FEATURE
<222> LOCATION: (1)..(34)
<223> OTHER INFORMATION: See Figure 3.
<300> PUBLICATION INFORMATION:
<301> AUTHORS: Russ, W.P., Lowery, D.M., Mishra, P., Yaffe, M.B., & Ranganathan R
<302> TITLE: Natural-like function in artificial WW domains
<303> JOURNAL: Nature
<304> VOLUME: 437
<306> PAGES: 579-83
<307> DATE: 2005

<400> SEQUENCE: 1

Arg Leu Pro Ala Gly Trp Glu Gln Arg Met Asp Val Lys Gly Arg Pro
1               5                   10                  15

Tyr Phe Val Asp His Val Thr Lys Ser Thr Thr Trp Glu Asp Pro Arg
            20                  25                  30

Pro Glu

<210> SEQ ID NO 2
<211> LENGTH: 34
<212> TYPE: PRT
<213> ORGANISM: Unknown
<220> FEATURE:
<223> OTHER INFORMATION: Natural WW domain also called Nedd4.3 Kanelis,
    V., Rotin D. & Forman-Kay, JD (2001) Solution structure of a Nedd4
    WW domain-ENaC peptide complex, Nat Struct Biol 8: 407-12.
<220> FEATURE:
<221> NAME/KEY: MISC_FEATURE
<222> LOCATION: (1)..(34)
<223> OTHER INFORMATION: See Figure 3.
<300> PUBLICATION INFORMATION:
<301> AUTHORS: Kanelis, V, Rothin, D., & Forman-Kay, J.D.
<302> TITLE: Solution structure of a Nedd4 WW domain ENaC peptide
    complex
<303> JOURNAL: Nat. Struct. Biol.
<304> VOLUME: 8
<306> PAGES: 407-12
<307> DATE: 2001

<400> SEQUENCE: 2

Pro Leu Pro Pro Gly Trp Glu Glu Arg Thr His Thr Asp Gly Arg Val
1               5                   10                  15

Phe Phe Ile Asn His Asn Ile Lys Lys Thr Gln Trp Glu Asp Pro Arg
            20                  25                  30

Met Gln

<210> SEQ ID NO 3
<211> LENGTH: 13
<212> TYPE: PRT
<213> ORGANISM: Homo sapiens
<220> FEATURE:
<221> NAME/KEY: MISC_FEATURE
<222> LOCATION: (1)..(13)
<223> OTHER INFORMATION: See Figure 3.
<300> PUBLICATION INFORMATION:
<301> AUTHORS: Russ, W.P., Lowery, D.M., Mishra, P., Yaffe M.B., & Ranganathan R.
<302> TITLE: Natural-like function in artificial WW domains
<303> JOURNAL: Nature
<304> VOLUME: 437

```
<306> PAGES: 579-583
<307> DATE: 2005
<313> RELEVANT RESIDUES IN SEQ ID NO: (1)..(13)

<400> SEQUENCE: 3

Glu Tyr Pro Pro Tyr Pro Pro Pro Pro Tyr Pro Ser Gly
1               5                   10

<210> SEQ ID NO 4
<211> LENGTH: 45
<212> TYPE: PRT
<213> ORGANISM: Artificial Sequence
<220> FEATURE:
<223> OTHER INFORMATION: Artificial sequence.
<220> FEATURE:
<221> NAME/KEY: MISC_FEATURE
<222> LOCATION: (1)..(45)
<223> OTHER INFORMATION: Combines a repeated set of hydrophilic spacers
      AGAGAGPEG with a fibronectin-derived RGDS cell-adhesion sequence.
      See Fig. 3.
<300> PUBLICATION INFORMATION:
<301> AUTHORS: Shen, W., Kornfield, JA, Tirrell, DA
<302> TITLE: Structure and mechanical properties of artificial protein
      hydrogels assembled through aggregation of leucine zipper peptide
      domains
<303> JOURNAL: Soft Matter
<304> VOLUME: 3
<306> PAGES: 99-107
<307> DATE: 2007
<313> RELEVANT RESIDUES IN SEQ ID NO: (1)..(9)
<300> PUBLICATION INFORMATION:
<301> AUTHORS: Petka, W.A., Harden, J.L., McGrath, K.P., Wirtz, D.,
      Tirrell, DA.
<302> TITLE: Reversible Hydrogels from Self-Assembling Artificial
      Proteins
<303> JOURNAL: Science
<304> VOLUME: 281
<306> PAGES: 389-392
<307> DATE: 1998-07-17
<313> RELEVANT RESIDUES IN SEQ ID NO: (1)..(9)
<300> PUBLICATION INFORMATION:
<301> AUTHORS: Guler, M.O., Hsu, L., Soukasene, S., Harrington, D.A.,
      Hulvat, J.F., Stupp, S.I.
<302> TITLE: Presentation of RGDS Epitopes on Self-Assembled Nanofibers
      of Branched Peptide Amphiphiles
<303> JOURNAL: Biomacromoleculses
<304> VOLUME: 7
<305> ISSUE: 6
<306> PAGES: 1855-1863
<307> DATE: 2006-05-19
<313> RELEVANT RESIDUES IN SEQ ID NO: (18)..(21)

<400> SEQUENCE: 4

Ala Gly Ala Gly Ala Gly Pro Glu Gly Ala Gly Ala Gly Ala Gly Pro
1               5                   10                  15

Glu Gly Arg Gly Asp Ser Ala Gly Pro Glu Gly Ala Gly Ala Gly Ala
            20                  25                  30

Gly Pro Glu Gly Ala Gly Ala Gly Ala Gly Pro Glu Gly
        35                  40                  45

<210> SEQ ID NO 5
<211> LENGTH: 45
<212> TYPE: PRT
<213> ORGANISM: Artificial Sequence
<220> FEATURE:
<223> OTHER INFORMATION: Artifical sequence
<220> FEATURE:
<221> NAME/KEY: MISC_FEATURE
<222> LOCATION: (1)..(45)
<223> OTHER INFORMATION: Combines repeated set of hydrophilic spacers
      AGAGAGPEG with a laminin-1 derived YIGSR binding protein sequence.
      See Figure 3
```

```
<400> SEQUENCE: 5

Ala Gly Ala Gly Ala Gly Pro Glu Gly Ala Gly Ala Gly Ala Gly Pro
1               5                   10                  15

Glu Gly Tyr Ile Gly Ser Arg Gly Pro Glu Gly Ala Gly Ala Gly Ala
            20                  25                  30

Gly Pro Glu Gly Ala Gly Ala Gly Ala Gly Pro Glu Gly
        35                  40                  45

<210> SEQ ID NO 6
<211> LENGTH: 18
<212> TYPE: PRT
<213> ORGANISM: Artificial Sequence
<220> FEATURE:
<223> OTHER INFORMATION: Artifical sequence
<220> FEATURE:
<221> NAME/KEY: MISC_FEATURE
<222> LOCATION: (1)..(19)
<223> OTHER INFORMATION: Previously described hydrophilic spacer
      AGAGAGPEG repeated twice. See Figure 3.

<400> SEQUENCE: 6

Ala Gly Ala Gly Ala Gly Pro Glu Gly Ala Gly Ala Gly Ala Gly Pro
1               5                   10                  15

Glu Gly

<210> SEQ ID NO 7
<211> LENGTH: 33
<212> TYPE: PRT
<213> ORGANISM: Escherichia coli
<220> FEATURE:
<221> NAME/KEY: MISC_FEATURE
<222> LOCATION: (1)..(33)
<223> OTHER INFORMATION: 6xHis tag produced as part of the recombinant
      protein production process in Escherichia coli .  See Fig 3.

<400> SEQUENCE: 7

Met Gly Ser Ser His His His His His His Ser Ser Gly Leu Val Pro
1               5                   10                  15

Arg Gly Ser Ser Ser Gly His Ile Asp Asp Asp Asp Lys Val Asp Gly
            20                  25                  30

Thr

<210> SEQ ID NO 8
<211> LENGTH: 253
<212> TYPE: PRT
<213> ORGANISM: Artificial Sequence
<220> FEATURE:
<223> OTHER INFORMATION: Artifical sequence for a hydrogel
<220> FEATURE:
<221> NAME/KEY: MISC_FEATURE
<222> LOCATION: (1)..(253)
<223> OTHER INFORMATION: Engineered sequence: N-terminal 6xHis Tag, WW
      Domain CC43, GTLDEL, Hydrophilic Spacer 1- RGDS site, ELLDGT, 1x
      to 5x repeated series of: [WW Domain CC43, GTLDEL, Hydrophobic
      Spacer 1-RGDS site, ELLDGT), WW Domain CC43, GTLE: see Fig. 3
<220> FEATURE:
<221> NAME/KEY: REPEAT
<222> LOCATION: (125)..(215)
<223> OTHER INFORMATION: Repeated between 1-5 times.  That is 1x, 2x,
      3x, 4x, and 5x are taught

<400> SEQUENCE: 8

Met Gly Ser Ser His His His His His His Ser Ser Gly Leu Val Pro
1               5                   10                  15

Arg Gly Ser Ser Ser Gly His Ile Asp Asp Asp Asp Lys Val Asp Gly
            20                  25                  30
```

```
Thr Arg Leu Pro Ala Gly Trp Glu Gln Arg Met Asp Val Lys Gly Arg
        35                  40                  45

Pro Tyr Phe Val Asp His Val Thr Lys Ser Thr Thr Trp Glu Asp Pro
    50                  55                  60

Arg Pro Glu Gly Thr Leu Asp Glu Leu Ala Gly Ala Gly Ala Gly Pro
65                  70                  75                  80

Glu Gly Ala Gly Ala Gly Ala Gly Pro Glu Gly Arg Gly Asp Ser Ala
                85                  90                  95

Gly Pro Glu Gly Ala Gly Ala Gly Ala Gly Pro Glu Gly Ala Gly Ala
            100                 105                 110

Gly Ala Gly Pro Glu Gly Glu Leu Leu Asp Gly Thr Arg Leu Pro Ala
            115                 120                 125

Gly Trp Glu Gln Arg Met Asp Val Lys Gly Arg Pro Tyr Phe Val Asp
        130                 135                 140

His Val Thr Lys Ser Thr Thr Trp Glu Asp Pro Arg Pro Glu Gly Thr
145                 150                 155                 160

Leu Asp Glu Leu Ala Gly Ala Gly Ala Gly Pro Glu Gly Ala Gly Ala
                165                 170                 175

Gly Ala Gly Pro Glu Gly Arg Gly Asp Ser Ala Gly Pro Glu Gly Ala
            180                 185                 190

Gly Ala Gly Ala Gly Pro Glu Gly Ala Gly Ala Gly Ala Gly Pro Glu
            195                 200                 205

Gly Glu Leu Leu Asp Gly Thr Arg Leu Pro Ala Gly Trp Glu Gln Arg
        210                 215                 220

Met Asp Val Lys Gly Arg Pro Tyr Phe Val Asp His Val Thr Lys Ser
225                 230                 235                 240

Thr Thr Trp Glu Asp Pro Arg Pro Glu Gly Thr Leu Glu
                245                 250

<210> SEQ ID NO 9
<211> LENGTH: 253
<212> TYPE: PRT
<213> ORGANISM: Artificial Sequence
<220> FEATURE:
<223> OTHER INFORMATION: Artificial hydrogel component
<220> FEATURE:
<221> NAME/KEY: MISC_FEATURE
<222> LOCATION: (1)..(253)
<223> OTHER INFORMATION: Engineered sequence: N-terminal 6xHis tag ,
      WW Domain N39, GTLDEL, Hydrophilic spacer 1-RDGS site, Hyrdophilic
      spacer 2, ELLDGT, 1x to 5x repeated (WW Domain N39, GTLDEL,
      Hyrdophilic spacer 1-RDGS site, ELLDGT), WW Domain N39, GTLE:
      see Fig. 3
<220> FEATURE:
<221> NAME/KEY: REPEAT
<222> LOCATION: (125)..(214)
<223> OTHER INFORMATION: Repeated from 1 to 5 times.  That is 1x, 2x,
      3x, 4x, and 5x are taught

<400> SEQUENCE: 9

Met Gly Ser Ser His His His His His His Ser Ser Gly Leu Val Pro
1               5                   10                  15

Arg Gly Ser Ser Ser Gly His Ile Asp Asp Asp Asp Lys Val Asp Gly
            20                  25                  30

Thr Pro Leu Pro Pro Gly Trp Glu Arg Thr His Thr Asp Gly Arg
        35                  40                  45

Val Phe Phe Ile Asn His Asn Ile Lys Lys Thr Gln Trp Glu Asp Pro
    50                  55                  60

Arg Met Gln Gly Thr Leu Asp Glu Leu Ala Gly Ala Gly Ala Gly Pro
```

```
                65                  70                  75                  80
    Glu Gly Ala Gly Ala Gly Ala Gly Pro Glu Gly Arg Gly Asp Ser Ala
                    85                  90                  95
    Gly Pro Glu Gly Ala Gly Ala Gly Ala Gly Pro Glu Gly Ala Gly Ala
                    100                 105                 110
    Gly Ala Gly Pro Glu Gly Glu Leu Leu Asp Gly Thr Pro Leu Pro Pro
                    115                 120                 125
    Gly Trp Glu Glu Arg Thr His Thr Asp Gly Arg Val Phe Phe Ile Asn
                    130                 135                 140
    His Asn Ile Lys Lys Thr Gln Glu Asp Pro Arg Met Gln Gly Thr Leu
    145                 150                 155                 160
    Asp Glu Leu Ala Gly Ala Gly Ala Gly Pro Glu Gly Ala Gly Ala Gly
                    165                 170                 175
    Ala Gly Pro Glu Gly Arg Gly Asp Ser Ala Gly Pro Glu Gly Ala Gly
                    180                 185                 190
    Ala Gly Ala Gly Pro Glu Gly Ala Gly Ala Gly Ala Gly Pro Glu Gly
                    195                 200                 205
    Glu Leu Leu Asp Gly Thr Pro Leu Pro Pro Gly Trp Glu Glu Arg Thr
                    210                 215                 220
    His Thr Asp Gly Arg Val Phe Phe Ile Asn His Asn Ile Lys Lys Thr
    225                 230                 235                 240
    Gln Trp Glu Asp Pro Pro Arg Met Gln Gly Thr Leu Glu
                    245                 250

<210> SEQ ID NO 10
<211> LENGTH: 136
<212> TYPE: PRT
<213> ORGANISM: Artificial Sequence
<220> FEATURE:
<223> OTHER INFORMATION: Artificial hydrogel component
<220> FEATURE:
<221> NAME/KEY: MISC_FEATURE
<222> LOCATION: (1)..(136)
<223> OTHER INFORMATION: Engineered sequence: N-terminal 6xHis Tag,
      Polyproline-rich Peptide PPxY, GTLDEL, Hydrophilic spacer 2,
      ELLDGT, 1x to 7x repeated (Polyproline-rich Peptide PPxY, GTLDEL,
      Hydrophilic spacer 2, ELLDGT), Polyproline-rich Peptide PPxY,
      GTLE:  see Fig.
<220> FEATURE:
<221> NAME/KEY: REPEAT
<222> LOCATION: (77)..(119)
<223> OTHER INFORMATION: Repeated from 1 to 7 times.  That is, 1x, 2x,
      3x, 4x, 5x, 6x, and 7x are taught

<400> SEQUENCE: 10

Met Gly Ser Ser His His His His His Ser Ser Gly Leu Val Pro
    1               5                   10                  15
    Arg Gly Ser Ser Gly His Ile Asp Asp Asp Lys Val Asp Gly
                    20                  25                  30
    Thr Glu Tyr Pro Pro Tyr Pro Pro Pro Tyr Pro Ser Gly Gly Thr
                    35                  40                  45
    Leu Asp Glu Leu Ala Gly Ala Gly Ala Gly Pro Glu Gly Ala Gly Ala
                    50                  55                  60
    Gly Ala Gly Pro Glu Gly Glu Leu Leu Asp Gly Thr Glu Tyr Pro Pro
    65                  70                  75                  80
    Tyr Pro Pro Pro Tyr Pro Ser Gly Gly Thr Leu Asp Glu Leu Ala
                    85                  90                  95
    Gly Ala Gly Ala Gly Pro Glu Gly Ala Gly Ala Gly Ala Gly Pro Glu
                    100                 105                 110
```

```
Gly Glu Leu Leu Asp Gly Thr Glu Tyr Pro Pro Tyr Pro Pro Pro
        115                 120                 125

Tyr Pro Ser Gly Gly Thr Leu Glu
    130             135
```

HETERO-ASSEMBLED HYDROGELS

CROSS-REFERENCE TO RELATED APPLICATIONS

This application claims priority from U.S. Provisional Application No. 61/060,144, filed on Jun. 10, 2008, which is incorporated herein by reference.

SEQUENCE LISTING

This application includes a sequence listing submitted in written form and in computer readable form on a compact disc.

FIELD OF THE INVENTION

The invention relates generally to hydrogels. In particular, the invention relates to viscoelastic hydrogels, methods of making viscoelastic hydrogels and methods of encapsulating cells, drugs, tissue, organs and the like in the viscoelastic hydrogels, and method of growing cells, tissue, organs and the like with the viscoelastic hydrogels.

BACKGROUND OF THE INVENTION

Cell transplantation is a proven method of treatment for certain immunological disorders and has shown promising effects for a variety of medical conditions including Parkinson's, Huntington's, stroke, spinal cord injury, myocardial infarction, and bone repair. Although a variety of transplanted progenitor cells and stem cells have had some degree of success in improving functional recovery, cell survival after transplantation is often poor and unpredictable, and has been directly correlated with functional outcome of the treatment in animal models. Therefore, there is a strong need to develop more reliable and efficient cell transplantation procedures.

Hydrogels are ideal materials for implantation because they introduce very low levels of foreign matter into the body and promote maximum diffusion of biomolecules throughout the scaffold due to their high water content. Hydrogel crosslinks can be either chemical, or physical. Since many chemical crosslinkers are toxic and result in non-injectable gels, physical hydrogels are preferred for many biomedical applications. Due to their unique structure, many physical hydrogels are shear-thinning, allowing them to be injected easily, an important criterion for non-invasive cell and drug delivery.

However, the assembly of polymers into physical hydrogels for cell encapsulation has mostly been governed by the use of external triggers. In these systems, cells are mixed with precursor macromolecules in the solution phase under specific environmental conditions. Following this, cells are encapsulated by exposure to a sudden change in pH, temperature, or ionic concentration to induce a solution to gel phase transition either in vitro or in situ. For example, common triggers for cell encapsulation by physical hydrogels include temperature sweeps from 4° C. to 37° C. for collagen and Matrigel; pH shifts from 2.0-2.5 to 7.4 for PuraMatrix and leucine-zipper systems; and cation concentration increases ranging from 20 to 200 mM for alginate and self-assembled peptide amphiphiles. These materials are generally designed to be in the gel phase at physiological conditions, requiring that cells be momentarily exposed to non-ideal environmental conditions in the sol phase (often a combination of low pH and temperature). Upon injection, the material equilibrates to physiological conditions and undergoes a phase change to the gel state. Because transplanted cells are highly sensitive to these non-physiological conditions, these triggers can be irreversibly detrimental to the encapsulated cells and accompanying proteins; and furthermore, these environmental conditions can be difficult to reproducibly control in a clinical setting. Therefore, current injection techniques within physical hydrogels can result in substantial loss of transplanted viable cells. This is of importance because cell viability and reproducibility in clinical settings have been directly correlated to the successful outcomes of these cell transplantation procedures. The present invention addresses at least some of the current problems and advances the art by introducing a physical hydrogel capable of encapsulating cells, drugs and proteins without subjecting them to variations in pH, temperature, or ionic strength.

SUMMARY OF THE INVENTION

The present invention provides a viscoelastic hydrogel based on the hetero-assembly of a first protein and a second protein when mixed under physiological conditions. The first protein includes a first association sequence and a first spacer. The second protein includes a second association sequence and a second spacer. The first association sequence and the second association sequence associate through hydrogen bonds to form physical crosslinks to form a three dimensional scaffold.

The first protein is represented by $\{1stA(1stSp)_m\}_x 1stA$, where 1stA is the first association sequence, 1stSp is the first spacer, m is 1 to 50, and x is 2 to 15. The second protein is represented by $\{2ndA(2ndSp)_n\}_y 2ndA$, where 2ndA is the second association sequence, 2ndSp is the second spacer, n is 1 to 50, and y is 2 to 15, and wherein m and n are non-integer multiples of one another.

In one example, the first association sequence is a WW protein sequence and the second protein is a polyproline-rich sequence. The first spacer is a first hydrophilic spacer protein sequence and the second spacer a second hydrophilic spacer protein sequence. In one example, the first hydrophilic spacer protein sequence and the second hydrophilic spacer protein sequence are not the same. In another example, the first hydrophilic spacer protein sequence and the second hydrophilic spacer protein sequence differ in the number of repetitions of each sequence (here the first and second spacer protein sequences can be the same or different sequences). In one example, the first hydrophilic spacer protein sequence is longer than the second hydrophilic spacer protein sequence.

BRIEF DESCRIPTION OF THE FIGURES

The present invention together with its objectives and advantages will be understood by reading the following description in conjunction with the drawings, in which:

FIGS. 5A-C show examples of assays for binding affinity of engineered protein components according to an embodiment of the invention. Binding isotherms for Component 1 variants, C3 ($K_d$=4.6±0.01 μM) or N3 ($K_d$=62±4.6 μM) with Component 2 variant P3 assayed by (FIG. 5A) tryptophan fluorescence quenching and (FIG. 5B, FIG. 5C) by isothermal titration calorimetry. Linkage of the association domains by hydrophilic spacers does not prevent molecular recognition, and choice of WW domain can tune the association energy.

(FIG. 6A) Mean-squared displacement of micron-sized fluorospheres embedded within individual solutions of C7 or P9 (6 wt %) or within a hydrogel made from a 1:1 mixture, C7:P9 (6 wt %) plotted on a log-log scale. (FIG. 6B, FIG. 6C) Mean-squared displacement of micron-sized fluorospheres embedded within 5 to 10 wt % hydrogels made from a 1:1 mixture of C7:P9 or N7:P9, respectively. Tuning the association energy through choice of WW domain directly alters the viscoelastic properties of the gel.

(FIGS. 9A-B) Total DNA quantification shows PC-12 and adult NPC proliferation on control substrates and C7:P9 and N7:P9 films for 5d. Data are shown as mean±standard deviation, N=6; * represents statistically significant differences (p<0.001); ANOVA followed by Tukey post-test.

DETAILED DESCRIPTION

Figure 1:
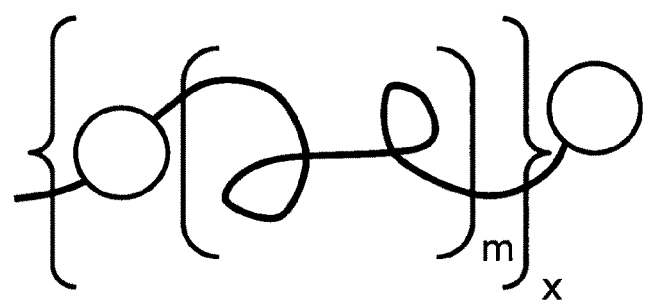
FIG. 1 shows an example of a two-component hydrogel system according to an embodiment of the invention.
Figure 1:
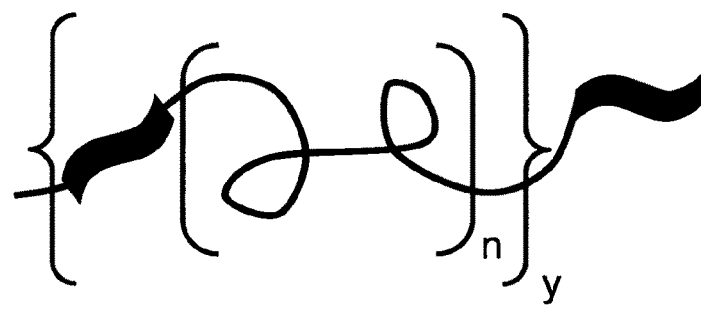

The embodiments presented in this invention relate to viscoelastic hydrogels (or "viscoelastic hydrogel scaffolds"), methods for making viscoelastic hydrogels, methods of encapsulating cells, drugs, tissue, organs, and the like, in the viscoelastic hydrogel, methods of growing cells, tissue, organs, and the like. Embodiments of this invention can be maintained in vivo, in vitro (e.g. in laboratory studies or diagnostics) as well as implanted in a host.

After fulfilling the purpose as the viscoelastic hydrogel, the viscoelastic hydrogel can dissolve or degrade, leaving nothing behind except the delivered drugs, proteins, or cells and/or the regenerated new cells, tissues, or organs. The methods of the invention permit the formation and preparation of structurally homogeneous viscoelastic hydrogels under physiological conditions. The mechanical and physical properties of the viscoelastic hydrogels can be controlled by controlling one or more parameters of the components used to form the viscoelastic hydrogel, which will be discussed in more detail infra.

The phrase "physiological conditions" refers to the range of solution conditions commonly encountered by cells, tissues, and organs in living hosts. For example, for humans, physiological conditions commonly refer to 37° C., a pH of about 7.4, and atmospheric pressure. These conditions will be specific to each particular host and may also vary for particular cells, tissues, and organs. The phrase "physiological buffer" refers to a buffered solution at physiological conditions. Examples of physiological buffers include, but are not limited to, phosphate-buffered saline (PBS) and Dulbecco's modified Eagle's medium (DMEM).

In general, embodiments of the viscoelastic hydrogel include a first protein and a second protein. The first protein and the second protein are each independently free flowing in a buffer solution or other solution at physiological conditions. The first protein includes a first association sequence and a first spacer. The second protein includes a second association sequence and a second spacer. When the two are mixed at physiological conditions, the first association sequence and the second association sequence bind together through noncovalent bonds (e.g., hydrogen bonds, van der Waal bonds, electrostatic bonds) to form physical crosslinks to form a three dimensional scaffold. In this regard, the first protein and the second protein hetero-assemble when mixed together. The term hetero-assembly is used to denote spontaneous assembly of different associating parts. Equivalent terms to hetero-assembly are bi-assembly or coupled-assembly to more specifically indicate that only two groups are associating as taught in the present invention.

The first protein and the second protein can be mixed together in a buffer solution or in another environment. In contrast to other hydrogels, embodiments of this invention can form a viscoelastic hydrogel without the need for crosslinkers, ultraviolet radiation, a catalyst, and/or sudden shifts in pH, ionic strength, and/or temperature. Embodiments of this invention can form a viscoelastic hydrogel in or at constant physiological conditions (e.g., in a physiological buffer solution having physiological conditions or in a host). The term "constant" in this context is used to distinguish from other hydrogel systems that change the pH, temperature, and the like to cause formation of the hydrogel.

Embodiments of this invention are advantageous over traditional synthetic chemistry for at least the following reasons. First, protein-based viscoelastic hydrogel scaffolds are composed entirely of amino acids and are therefore biodegradable and have displayed good biocompatibility. Second, using genetic templates to synthesize the viscoelastic hydrogel scaffold material affords absolute control over the molecular-level design, allowing systematic optimization of the scaffold properties. Third, peptide sequences derived from the extracellular matrix are directly incorporated into the viscoelastic hydrogel scaffold to mimic the natural extracellular matrix of cells, enhancing cell adhesion, viability, and migration. Unlike currently available hydrogels for cell culture experiments and medical therapies, embodiments of the viscoelastic hydrogel system do not require chemical crosslinkers or shifts in environmental conditions to induce gelation. Embodiments of the viscoelastic hydrogel can encapsulate cells, tissues, organs, drugs, and proteins at constant physiological conditions, therefore, embodiments of the present disclosure are highly biocompatible.

Embodiments of the viscoelastic hydrogels of this invention are useful in any situation in which a hydrogel is useful. In an embodiment, the viscoelastic hydrogel can be used to encapsulate and/or grow cells or cell cultures of a single type or multiple types, tissues, and/or organs. In an embodiment, the cells may be integrated with the viscoelastic hydrogel using a variety of methods. For example, the viscoelastic hydrogel may be submersed in an appropriate growth medium for the cells of interest, and then directly exposed to the cells. The cells are allowed to proliferate on the surface and migrate into and through the viscoelastic hydrogel. The viscoelastic hydrogel is then removed from the nutrient medium (which can vary depending on cell type), washed if necessary, and implanted.

In another embodiment, the cells of interest are dispersed into an appropriate solution (e.g., a growth medium or buffer) that contains either the first protein or the second protein; the solution will be a freely flowing liquid. Then, the other of the first protein or the second protein is added to the solution, causing the formation of a three dimensional, viscoelastic hydrogel. This hydrogel/cell construct can be directly injected into a host using a syringe or implanted into the host.

In another embodiment, the cells of interest are dispersed into an appropriate solution (e.g., a growth medium or buffer) that contains either the first protein or the second protein. This freely flowing solution can be loaded into a syringe (either single barrel or double barrel) and injected into the host as a freely flowing solution. Injection of the other of the first protein or the second protein can be simultaneous (through use of a double barrel syringe) or subsequent (through use of a second single barrel syringe) to induce gelation within the host.

The cells that may be incorporated on or into the viscoelastic hydrogel include, but are not limited to, stem cells, precursor cells, smooth muscle cells, skeletal myoblasts, myocardial cells, endothelial cells, endothelial progenitor cells, bone-marrow derived mesenchymal cells, genetically modified cells, neurons, and the like.

In another embodiment, the viscoelastic hydrogels of this invention can be used to make implantable medical devices where the viscoelastic hydrogel portion(s) of the device includes biologically active molecules (e.g., compositions useful for treating a disease in a mammal, compositions useful for ensuring acceptance of the device, and the like). In an embodiment, the biologically active molecules are released from the viscoelastic hydrogel after the device is implanted into a living body. Thus, these embodiments of implantable medical devices can be used, for example, as drug delivery devices that release a specific dosage of a drug that is effective to ameliorate the symptoms of a disease in a living body, such as a mammalian body (e.g., a human body).

An embodiment of this invention provides for methods for forming a viscoelastic hydrogel at a site of application. The methods for forming a viscoelastic hydrogel at a site of application include combining a first component and a second component at the site of application to form a viscoelastic hydrogel at physiological conditions. In an embodiment, the viscoelastic hydrogel is formed at the site of a wound in a living body, such as a host (e.g., a human body). The viscoelastic hydrogel may fill in, or repair, a missing or damaged portion of tissue, and/or may deliver biologically active molecules (e.g., therapeutic agents) to a damaged portion of a living body, thereby promoting wound healing. In some embodiments, the methods may be used to apply stem cells (or other cells), included within one or both of the first component or the second component used to form the viscoelastic hydrogel or disposed after formation of the viscoelastic hydrogel, to a damaged portion of a living body. The stem cells thereafter divide and differentiate to form cells, tissue, or the like, that repair the damaged portion of the living body.

Viscoelastic Hydrogel Components and Structure

As noted above, the viscoelastic hydrogel includes a first protein and a second protein. The first protein and the second protein are each independently free flowing in a buffer solution at physiological conditions. The first protein includes a first association sequence and a first spacer. The second protein includes a second association sequence and a second spacer. When the two are mixed at physiological conditions, the first association sequence and the second association sequence bind through secondary, physical bonds (e.g., hydrogen bonds, electrostatic interactions, dipole-dipole bonds) with a specified stoichiometry. These associating sequences form physical crosslinks that link the proteins into a network that form a three-dimensional viscoelastic hydrogel. In this regard, the first protein and the second protein hetero-assemble to form the viscoelastic hydrogel when mixed together. The first protein and the second protein can be mixed together in a buffer solution or in another environment.

In an embodiment of the present disclosure, a cell-binding peptide can be associated with (attached directly or indirectly) the viscoelastic hydrogel or with the first protein and/or the second protein prior to forming the viscoelastic hydrogel. In an embodiment, the cell-binding peptide is incorporated into the first spacer and/or the second spacer. Table 1 includes a listing of some exemplary cell-binding peptides and their putative receptors.

TABLE 1

Examples of cell-binding peptides for inclusion in hetero-assembling hydrogels. List modified from Table I in "Functional peptide sequences derived from the extracellular matrix glycoproteins and their receptors: Strategies to improved neuronal regeneration" by Sally Meiners, Mary Lynn T. Mercado and published in Molecular Neurobiology 2003-27(2): 177-195.

| Peptide | Molecular Origin | Domain or Region | Putative Receptor |
|---|---|---|---|
| VFDNFVLK | Tenascin-C | fnD | α7β1 integrin |
| EIDGIELT |  | fzn3 | α9β1 integrin |
| RGD |  | fn3 | α8β1, αvβ3 integrins |
| RGD | Fibronectic | fn10 | α3β1, α5β1, α7β1, α8β1, αvβ1, αvβ3, αvβ6 integrins |
| LDV |  | IIICS-CSI | α4β1 integrin |

TABLE 1-continued

Examples of cell-binding peptides for inclusion in hetero-assembling hydrogels. List modified from Table I in "Functional peptide sequences derived from the extracellular matrix glycoproteins and their receptors: Strategies to improved neuronal regeneration" by Sally Meiners, Mary Lynn T. Mercado and published in Molecular Neurobiology 2003-27(2): 177-195.

| Peptide | Molecular Origin | Domain or Region | Putative Receptor |
|---|---|---|---|
| REDV | | IIICS-CSV | α4β1 integrin |
| EDGIHEL | | EDA | α4β1, α9β1 integrins |
| RDIAEIIKDI | Laminin-1 | γ 1 chain | Unidentified G-protein coupled receptor |
| IKVAV | | α 1 chain | β-amyloid precursor protein(APP) |
| YIGSR | | β 1 chain | 67 kDa YIGSR-binding protein |
| IKLLI | | α 1 chain | α3β1 integrin |
| RGD | | α 1 chain | α6β1, αvβ3 integrins |
| RKRLQVQLSIRT | | α 1 chain | |
| KNRLTIELEVRT | Laminin-2 | α 1 chain | |
| LRE | s-Laminin | α 2 chain | |

In an embodiment, the cell-binding peptide can be used to bind to the cells integrated in the viscoelastic hydrogel. In another embodiment, the cell-binding peptide can be used to bind to cells or tissue at the place of introduction to the host. In yet another embodiment, the viscoelastic hydrogel can include multiple types of cell-binding peptides having different purposes or resulting in synergistic effects.

The first protein is represented by $\{1stA(1stSp)_m\}_x 1stA$, where:
1stA is the first association sequence,
1stSp is the first spacer, and
m is 1 to 50, and x is 2 to 15.

The second protein is represented by $\{2ndA(2ndSp)_n\}_y 2ndA$, where:
2ndA is the second association sequence,
2ndSp is the second spacer, and
n is 1 to 50, and y is 2 to 15.

For both x and y, 2 is the minimum number required to form an interconnected network. The subscripts m and n are non-integer multiples of one another. FIG. 1 is a schematic of an embodiment of the first protein (shown as protein A) and the second protein (shown as protein B). The circle is the first association sequence and the looped line in the parentheses with the subscript m is the first spacer. The tilde symbol is the second association sequence and the looped line in the parentheses with the subscript n is the second spacer.

Table 2 illustrates a number of variables that can affect one or more properties of embodiments of the viscoelastic hydrogel. In addition, Table 2 illustrates the effects that each variable has on the viscoelastic hydrogel. It should be noted that one or more of the variables can be adjusted for an embodiment of the viscoelastic hydrogel to vary one or more of the properties of the viscoelastic hydrogel.

TABLE 2

Examples of variables affecting the properties of the hetero-assembling hydrogels.

| Component | Variables | Effect on Hydrogel Properties |
|---|---|---|
| Protein A and B association domains | A:B or B:A stoichiometry | Increasing the A:B or B:A stoichiometry above 1:1 yields stiffer gels |
| | A:B kinetic association on-rate, $k_{on}$ | Larger $k_{on}$ (ie, faster association rates) yield faster gelation times |
| | A:B kinetic association off-rate, $k_{off}$ | Larger $k_{off}$ (ie, faster dissociation rates) yield faster relaxation and erosion times |
| | A:B thermodynamic dissociation constant, $K_d$ | Smaller $K_d$ (where $K_d = k_{off}/k_{on}$) yields stiffer gels with more equilibrium crosslinks and slower erosion times |
| | Number of A and B association domains per molecule (x + 1 and y + 1) | More association domains per molecule yield stiffer hels with slower erosion times |
| Hydrophylic spacer domains | Length of spacer sequence in component A (m) | Longer chains promote chain entanglement and slower relaxation and erosion times |
| | Length of spacer sequence in component B (n) | Longer chains promote chain entanglement and slower relaxation and erosion times |
| | Relative ratio of spacer sequences (m/n) | Non-integer ratios promote efficient gelation by preventing multiple crosslinks between the exact same two molecular chains |
| Cell-binding peptides (can be included within the hydrophilic spacers of Component A and/or Component B) | Identity of binding peptide | Determines which cell types can bind to the gel and the strength of binding |
| | Number of binding peptides including in each spacer domain | Alters the cell signaling |
| | Location of binding peptides included in each spacer domain | Alters the cell signaling |

Embodiments of the first association sequence or the second association sequence are selected from proteins that at physiological conditions can associate (hetero-assemble) with one another through non-covalent bonds (e.g., hydrogen bonds, van der Waal bonds, electrostatic bonds) to form physical crosslinks to form a three dimensional scaffold. In general, the first association sequence and the second association sequence have sequences that allow them to fold into a specific conformation and to interact with each other physically through specific, non-covalent secondary bonds. Both the first and second association sequences should not be able to hetero-associate with themselves. Both the first and second association sequences must be suitable for synthesis using recombinant molecular biology techniques.

Other variables to be considered when choosing appropriate association sequences are listed in Table 2 along with their effects on the hydrogel properties. The first and second association sequences may bind together with 1:1 stoichiometry; increasing the stoichiometry ratio will increase the relative stiffness of the resulting hydrogel. Association sequences with varying kinetics and thermodynamics of binding will tune the resulting viscoelastic properties of the hydrogel. For example, association sequences with larger on-rates, $k_{on}$, will have faster association rates and yield materials with faster gelation times. Association sequences with larger off-rates, $k_{off}$, will have faster dissociation rates and yield materials with faster relaxation and erosion times. Association sequences with smaller thermodynamic equilibrium dissociation constants, $K_D$ (where $K_D = k_{off}/k_{on}$), will yield stiffer gels with more equilibrium crosslinks and slower erosion times.

In an embodiment, one of the first association sequence or the second association sequence can be a WW block copolymer and the other of the first association sequence or the second association sequence can be a polyproline-rich peptide (See Example for more details). These two association sequences were selected for one or more of the following criteria: i) The interactions between the WW domain and the polyproline-rich peptide are well understood and can be tuned across a range of dissociation constants. The reversible association of these two sequences when mixed together will provide the transient physical crosslinks that allow the scaffold to form a hydrogel. ii) The WW domain forms a robust fold (a short triple-stranded anti-parallel beta-sheet secondary structure) and has been successfully expressed in and purified from *E. coli* fermentation. iii) These domains naturally occur intracellularly therefore, they are not expected to interfere with external cellular signaling if they are presented to the cells as part of an extracellular hydrogel scaffold.

Separately, these two components form free flowing solutions in physiological buffer; however, upon mixing, the WW domains will associate with the polyproline-rich peptides through hydrogen bonding to form physical crosslinks between chains. By varying the dissociation constant between the two proteins, the number of repeating WW or PP blocks per chain, or the length of the hydrophilic spacer, we are able to tune the time-dependent hydrogel rheology. Additional details are described in Examples.

Embodiments of the first spacer and the second spacer can be selected from hydrophilic spacer protein sequences. The first spacer and the second spacer are not required to be the same protein domains (but can be the same if desired, just repeated a different number of times). In an embodiment, one of the first spacer and second spacer may be longer than the other to accommodate the different length and/or folding of the first association sequence and/or the second association sequence. In an embodiment, the first spacer and/or second spacer can be selected to modify one or more of the characteristics of the viscoelastic hydrogel scaffold. In another embodiment, the first spacer and/or second spacer can include a cell-binding peptide, such as those noted above.

In general, the selection of the first spacer and/or second spacer can be conducted to accommodate the formation of the viscoelastic hydrogel scaffold. Choosing longer spacer sequences will promote chain entanglement and slower relaxation and erosion times (FIG. 1 and Table 2).

Figure 3:
FIG. 3 shows an example of the design, construction, and expression of WW Block Copolymers (C[x+2] or N[y+2]) and PolyProline-Rich Peptide Chains (P[z+2]) according to an embodiment of the invention. The figure shows the amino acid sequences of the two WW domains, a polyproline-rich peptide, and the hydrophilic spacers used in the design and construction of Components 1 and Components 2 of our physical hydrogel.

In an embodiment, the length of the first spacer was chosen to form a random coil with an estimated diameter equal to 1.5 times the length of a folded WW domain, AGAGAGPE-GAGAGAGPEG (e.g. see FIG. 3, SEQ ID No:6). The second spacer was chosen to be a non-integer multiple in length (5/2 times the length of the first spacer) to prevent multiple association sites on one molecule of component A from interacting with multiple association sites on one molecule of component B (i.e., to prevent two molecules from "zipping" up). In this same example, the RGD amino acid cell-binding peptide was included in the second spacer.

In an embodiment, any other known cell-binding peptide can be included in either the first and/or second spacers. Examples of known cell-binding peptides are listed in Table 1.

In an embodiment, multiple cell-binding peptides can be included in a single spacer domain or in various combinations of the spacer domains. Varying the number and identity of cell-binding peptides in the spacer domains can be used to control the density of cell-binding events that can occur between the hydrogel and an integrated cell.

The hydrophilic spacer can be any sequence known to form a random coil that links together multiple association domains and promotes water solubility. An alternative example of a hydrophilic spacer sequence is repeats of the peptide sequence GGGS. The overall number of repeats of the association domain and the hydrophilic spacer sequence can also be tuned for both components (Table 2 and FIG. 1). Including more repeats of an association domain per single molecular chain will yield stiffer gels with slower erosion times.

Methods of Making the Viscoelastic Hydrogel

The invention includes methods of making viscoelastic hydrogels. In general, the first protein and the second protein can be mixed under physiological conditions to form a viscoelastic hydrogel.

In an embodiment, the first protein and the second protein can be mixed under physiological conditions in a buffer solution that is at physiological conditions. Embodiments of the buffer solution include, but are not limited to, phosphate buffered saline, Dulbecco's modified Eagle's medium, and other known mammalian cell culture media. The first protein and the second protein can be mixed in the buffer solution and are about 1-20% by weight of the mixture.

In another embodiment, the first protein and the second protein can be mixed in a host or at a position within a host, where the conditions for the mixture are at physiological conditions. In an embodiment, the first protein and the second protein can be mixed at the site of an injury or procedure (e.g., operation).

In an embodiment, one or more types of cells can be added to the viscoelastic hydrogel after it is formed, while in another embodiment, one or more types of cells can be added to one or both of the first protein or the second protein prior to forming the viscoelastic hydrogel. In an embodiment, one or more cells can be added prior to and after the formation of the viscoelastic hydrogel.

In an embodiment, appropriate nutrients can be added to the viscoelastic hydrogel before or after formation of the viscoelastic hydrogel and/or before or after addition of one or more types of cells.

Kits

The invention also provides the first protein and the second protein, and directions of use. In addition, embodiments of the present disclosure can include buffers and other components to assist in using embodiments of the present invention.

EXAMPLES

Now having described the embodiments of the invention, in general, the following example describes some additional embodiments. While embodiments of the invention are described in connection with the example and the corresponding text and figures, there is no intent to limit embodiments of the invention to these descriptions. On the contrary, the intent is to cover all alternatives, modifications, and equivalents included within the spirit and scope of embodiments of the present disclosure.

Figure 2:
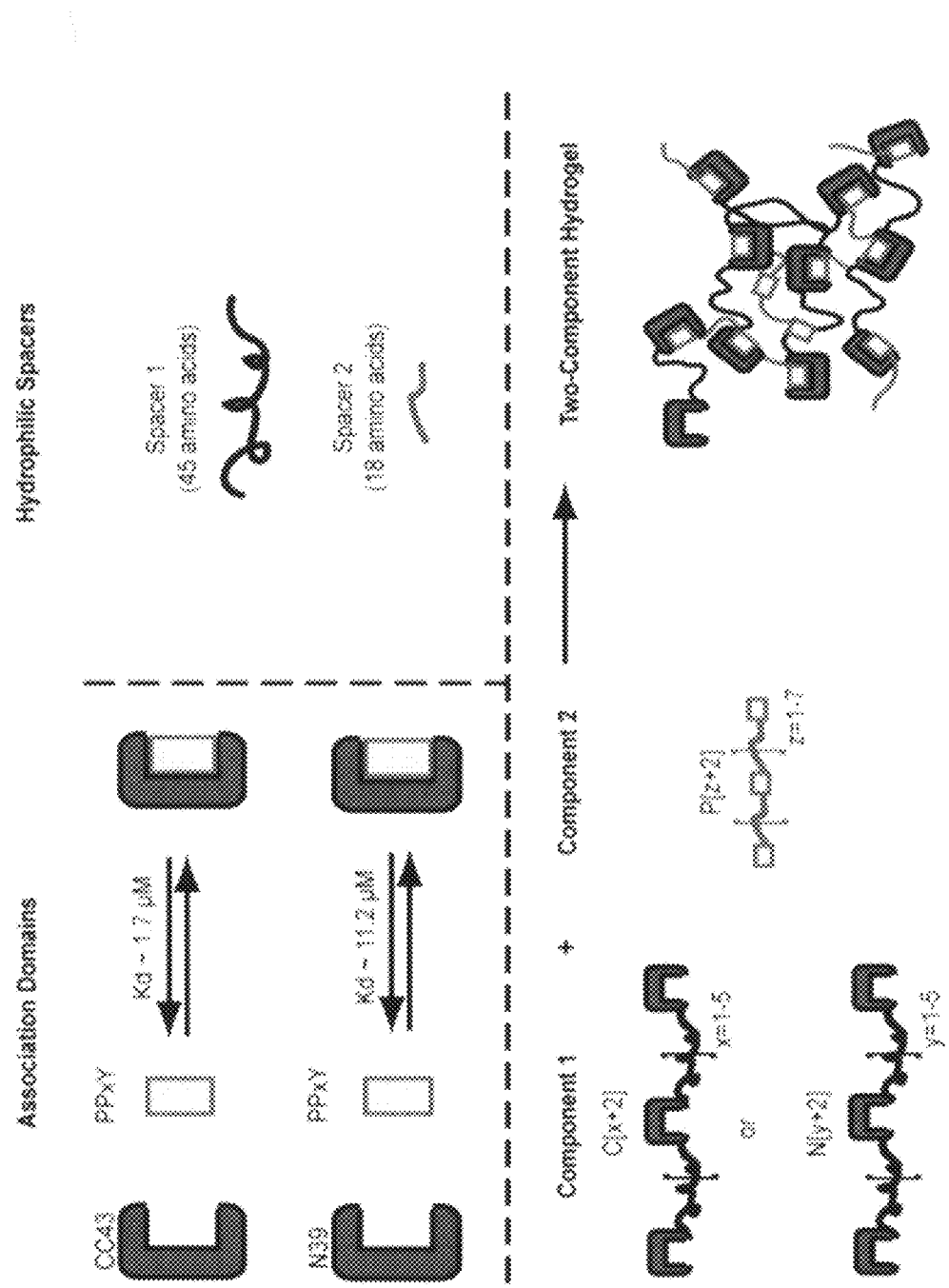
FIG. 2 shows an example of a design of the two-component, molecular-recognition hydrogel. Upper left panel: Modular association domains that assemble through molecular recognition. Both WW domains (CC43 and Nedd4.3) bind the same polyproline peptide (PPxY). Upper right panel: Hydrophilic spacers of varying lengths are used to link multiples repeats of WW domains (Spacer 1) or polyproline peptides (Spacer 2). Lower panel: Three engineered protein families: C[x+2], N[y+2], and P[z+2], made of multiple repeats of CC43, Nedd4.3, and PPxY, respectively. Mixing Component 1 (either C[x+2] or N[y+2]) with Component 2 at constant physiological conditions results in hydrogel formation via specific molecular-recognition interactions.

In this example, we utilized the concept of protein-protein interactions between specific peptide domains to design a two-component, molecular-recognition physical hydrogel system. The two components each contain separate peptide domains that associate together upon mixing under constant physiological conditions (FIG. 2). Therefore, this two-component hetero-assembly strategy is tailor-made to encapsulate cells and proteins without subjecting them to variations in pH, temperature, or ionic strength. This assembling strategy should make the system easy to use and clinically friendly as the gel will form simply upon mixing of the two components, similar to the formation of two-component polymeric epoxies.

Three criteria were used to select the association domains for our engineered proteins. First, their amino acid sequences must be short to allow multiple domains to be repeated in a single polymer that expresses well in a recombinant host. Second, the domains must be naturally found intracellularly so as not to interfere with external cell signaling when presented as part of a hydrogel matrix. Third, the domain association should be stable and tunable. The WW domain and the proline-rich peptide, two small peptide domains that associate together, were found to meet these criteria. The WW domain (~31-40 amino acids) adopts an anti-parallel, triple-stranded β-sheet conformation and has shown surprising specificity and affinity for proline-rich peptides despite its non-conserved sequences. Many WW domain sequences have been identified in nature and derived computationally. In this example, we chose two WW domains, the computationally-derived CC43 (Russ, W. P., Lowery, D. M., Mishra, P., Yaffe, M. B. & Ranganathan, R. (2005)*Natural-like function in artificial WW domains. Nature* 437.579-83) and the wild-type sequence Nedd4.3 (Kanelis, V, Rotin, D. & Forman-Kay, J. D. (2001) *Solution structure of a Nedd4 WW domain-ENaC peptide complex. Nat Struct Biol* 8:407-12; Russ, W. P., Lowery, D. M., Mishra, P., Yaffe, M B. & Ranganathan, R. (2005) *Natural-like function in artificial WW domains. Nature* 437-579-83) (Protein Data Bank 1I5H), reported to differ by an order of magnitude in their association constants with group I proline-rich peptides (PPxY). Multiple repeats of each association domain were linked together with random coil hydrophilic spacers to form three separate families of engineered recombinant proteins with varying chain lengths (FIGS. 2-3). The hydrophilic spacers were hypothesized to add flexibility to the protein chains, thereby facilitating accessibility and binding between the WW and PPxY domains. We designed the length of hydrophilic spacer 1, which links multiple WW domains, to be equal to or greater than the length of a single WW domain (~25 Å based on X-ray crystallography) assuming the spacer has a self-avoiding random coil configuration. The length of hydrophilic spacer 2, which links multiple PPxY domains, was chosen to be a non-integer multiple (2/5) of spacer 1 to minimize the possibility of several physical crosslinks forming between a single component 1 chain and a single component 2 chain, i.e., "zipping up" of pairs of molecules, which would prevent formation of a fully linked network.

Results

Figure 4A:
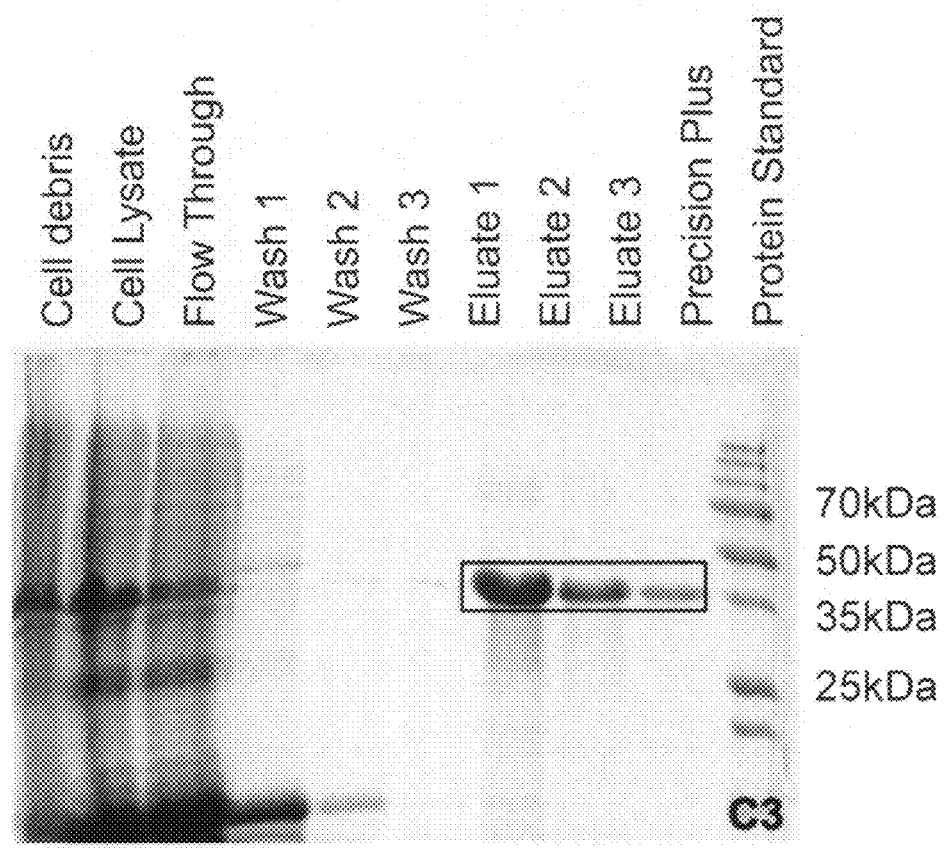
FIGS. 4A-C show examples of SDS PAGE electrophoresis showing the expression and purification of C3 (FIG. 4A), N3 (FIG. 4B), and P3 (FIG. 4C). C[x+2], N[y+2], and P[z+2] that were successfully expressed in *Escherichia coli* BL21(DE3) host strain (Novagen, San Diego, Calif.) upon induction with 0.5 mM isopropyl β-D-1-thiogalactopyranoside (IPTG). The recombinant proteins were purified via specific binding of their 6× His tag to Ni-NTA resin (Qiagen, Valencia, Calif.). The apparent molecular weights as observed by SDS gel electrophoresis are significantly larger than the actual molecular weights. The low mobility of these proteins can be explained by the highly acidic and hydrophilic nature of the spacers, which bind the anionic surfactant SDS weakly, resulting in a reduced overall effective charge in the electrophoretic separation process. Molecular weights were confirmed by MALDI-MS.
Figure 4B:
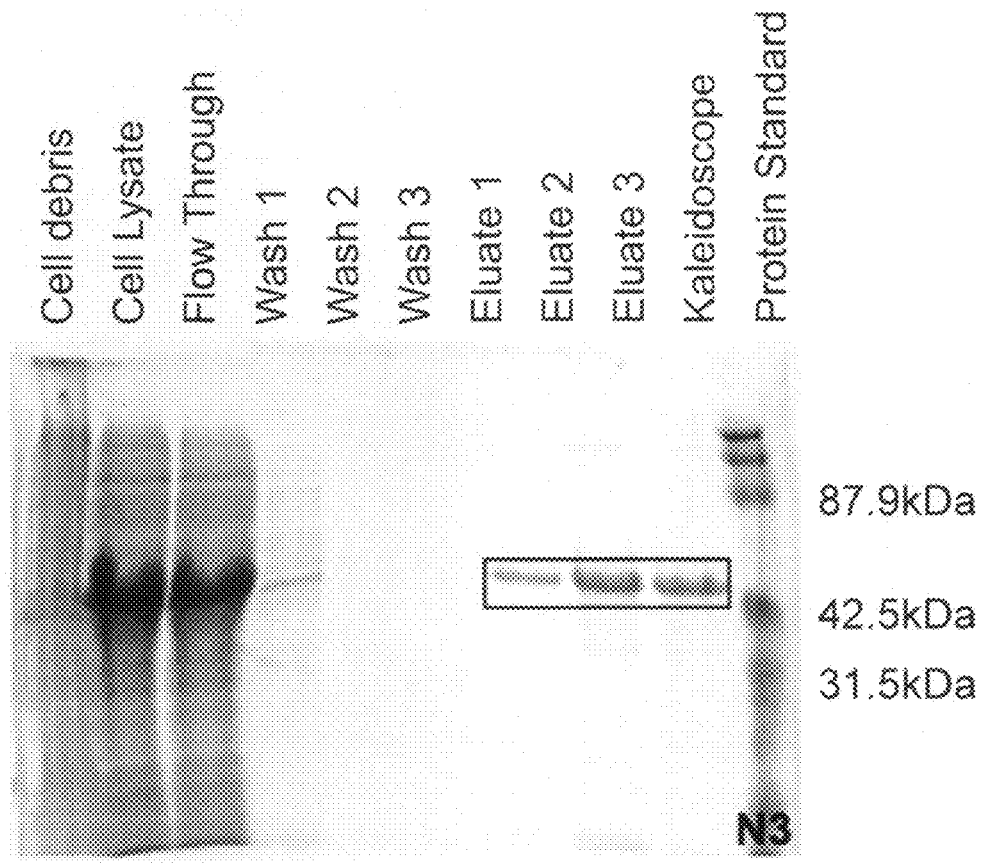
Figure 4C:
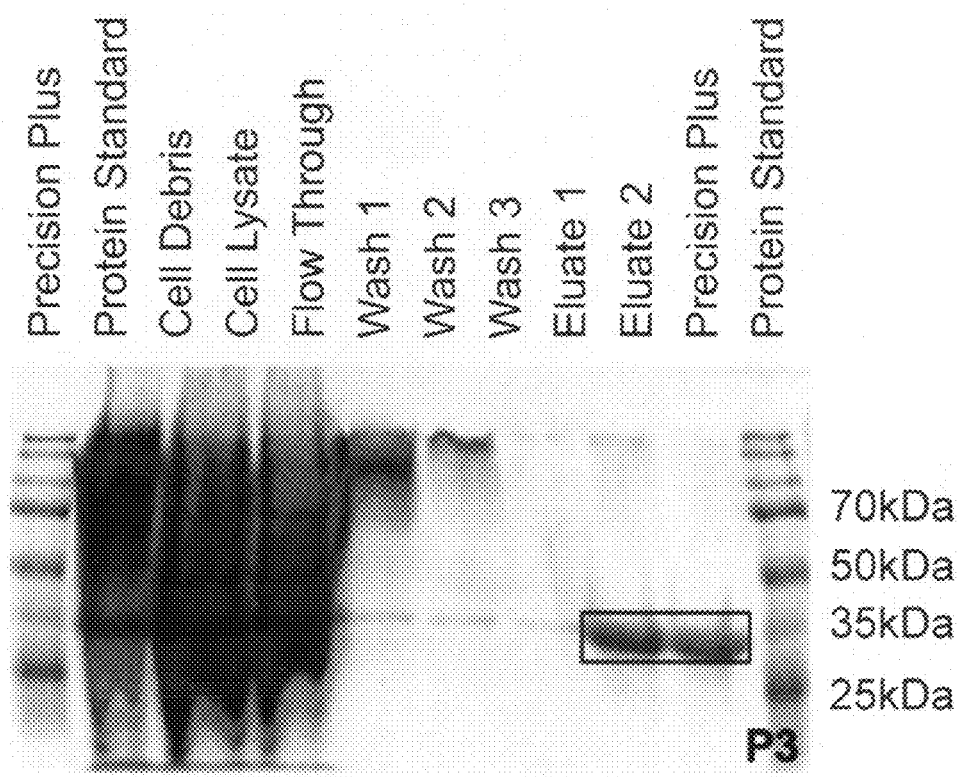
Figure 5A:
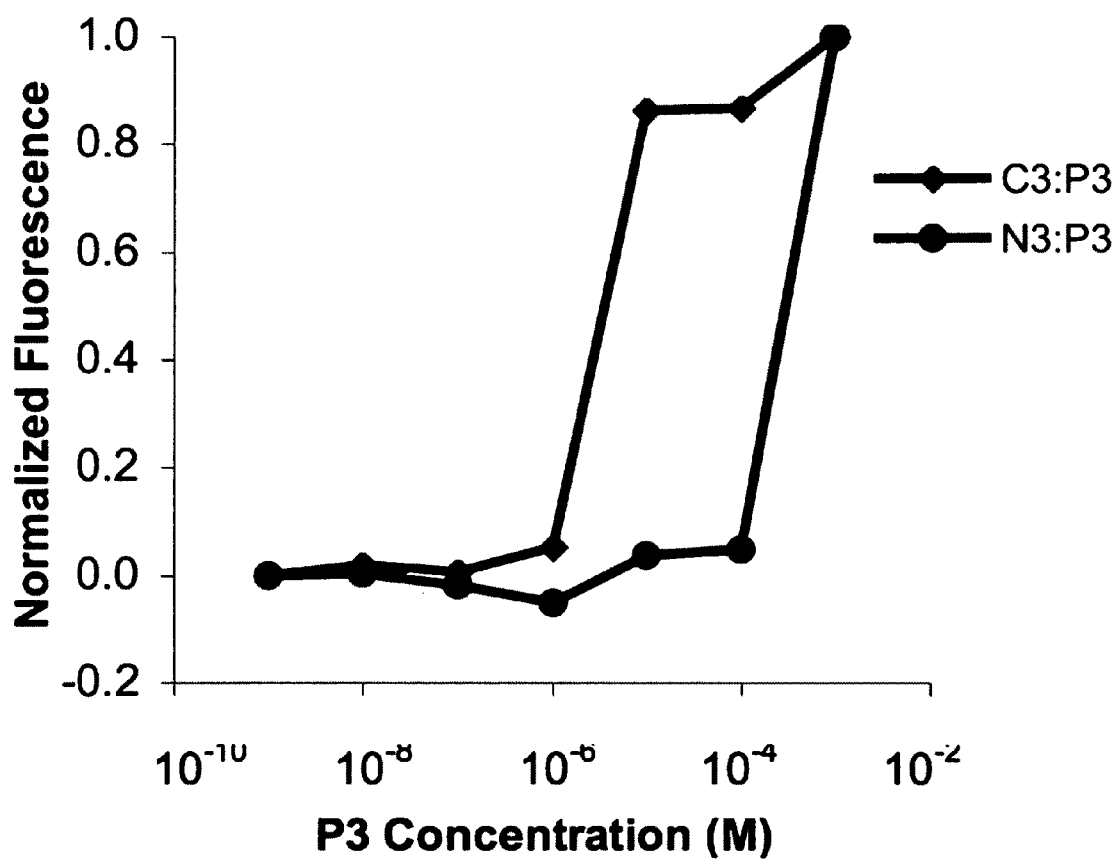

The synthesis of these precisely designed polymers was achieved using recombinant protein technology to encode each primary sequence in an exact modular genetic construct. The engineered proteins were successfully expressed in *Escherichia coli* and purified via affinity chromatography (FIGS. 4A-C). To verify that the association domains properly fold and bind when fused to hydrophilic spacers on their C- and N-termini, secondary structure and binding analyses were performed on protein-polymers with three repeats of each domain (C3, N3, and P3). Circular dichroism of C3 and N3 showed the characteristic features associated with the anti-parallel, triple-stranded β-sheet fold of a WW domain. Binding affinities were measured by isothermal titration calorimetry and tryptophan fluorescence quenching experiments (FIGS. 5A-C). P3 binds to C3 and N3 with apparent dissociation constants of $4.6 \pm 0.01$ μM and $62 \pm 4.6$ μM, respectively, consistent with previous observations of monomeric units of CC43 and Nedd4.3 bound to a model group I polyproline peptide (apparent dissociation constants of $1.7 \pm 0.1$ μM and $11.2 \pm 1.2$ μM, respectively) (FIGS. 5B-C). These assays demonstrate that the modular approach to protein engineering allows for the systematic design of families of proteins that physically bind through precise molecular-recognition interactions with tunable association energies.

Figure 6A:
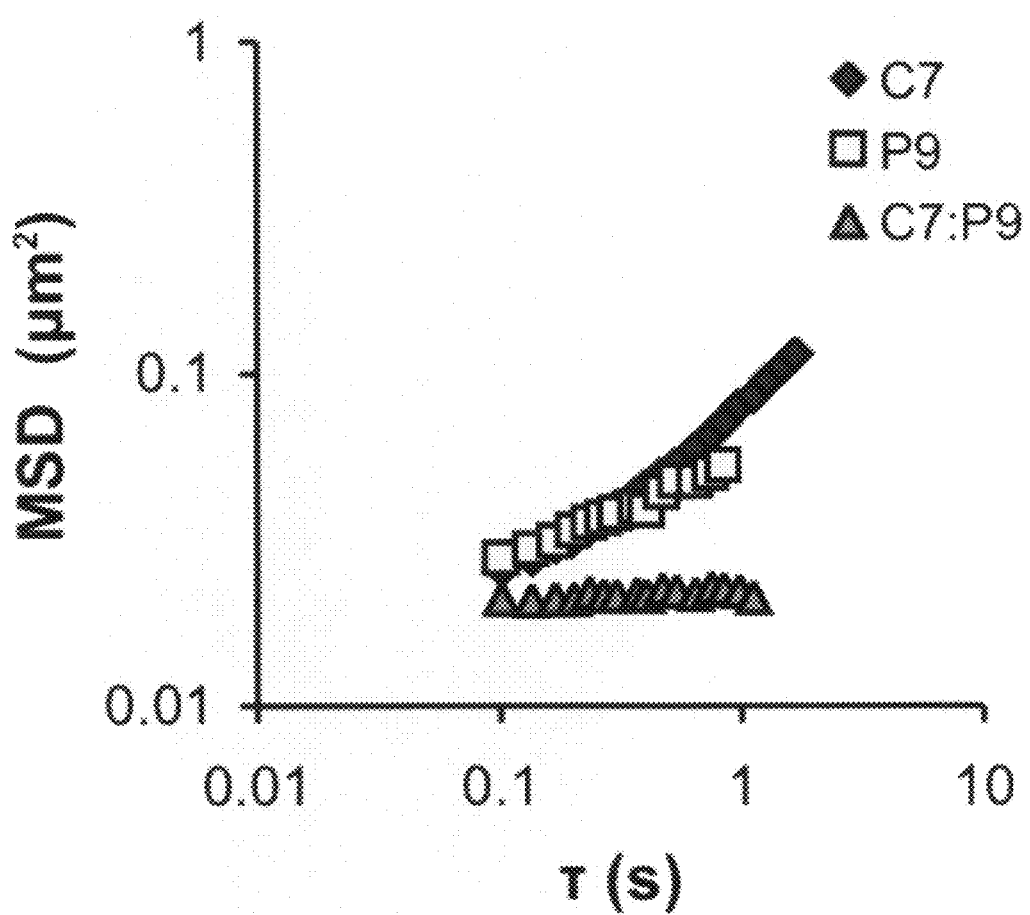
FIGS. 6A-C show examples of microrheological characterization of the two-component hydrogels according to an embodiment of the invention.
Figure 6B:
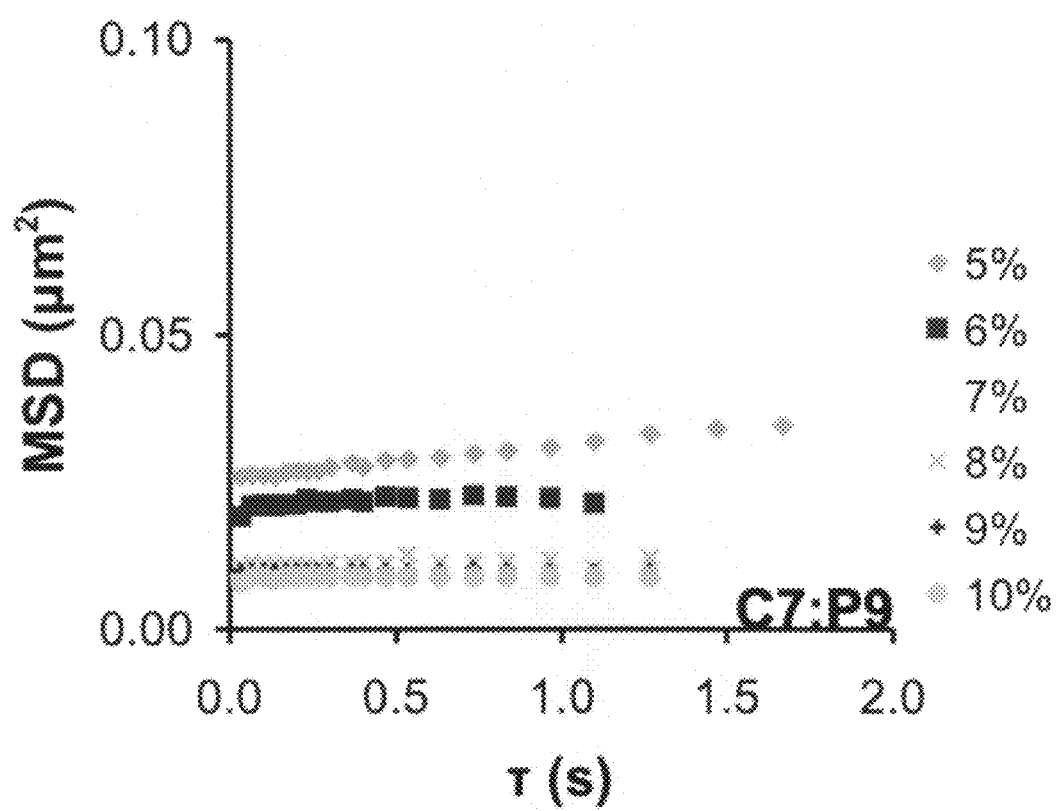
Figure 6C:
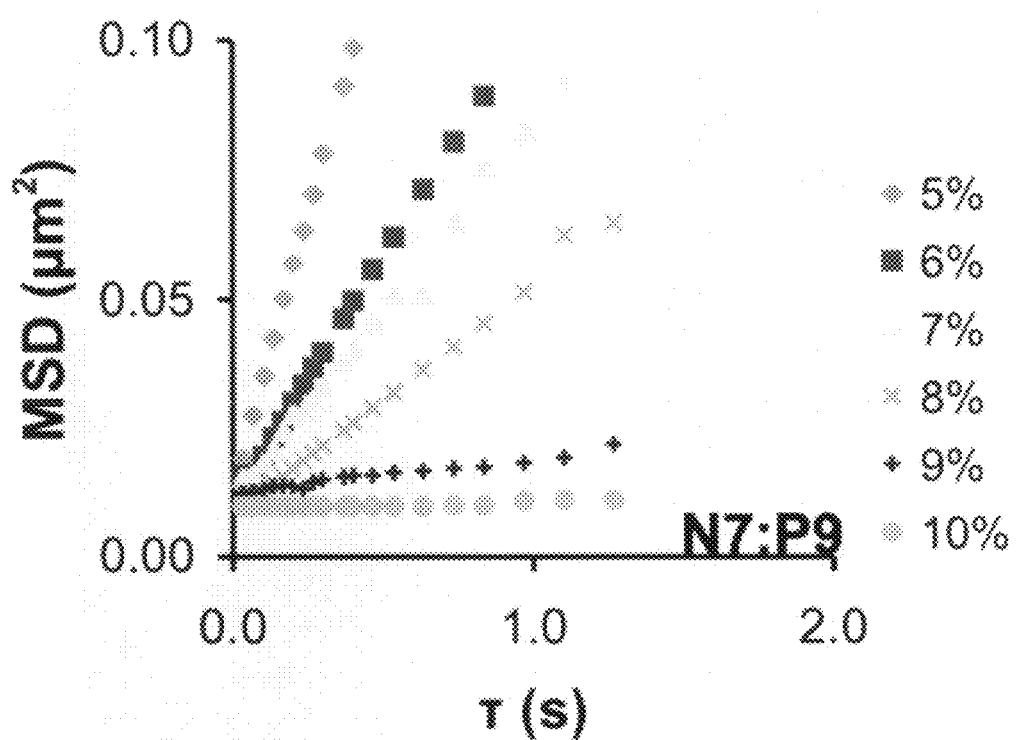

While the three-peat polymers (C3, N3, and P3) did not form gels upon association, we argued that increasing the number of potential physical crosslinks per chain by synthesizing polymers with higher numbers of repeats (C7, N7, and P9) would result in the formation of bulk hydrogels. Simple mixing of a solution of C7 (6 wt %) with a solution of P9 (6 wt %) at constant physiological pH, temperature, and ionic strength leads to the formation of a viscoelastic hydrogel, C7:P9, as confirmed via particle tracking of micron-sized fluorospheres embedded within the hydrogel networks (FIG. 6A). The mean-squared displacement (MSD) of fluorospheres within solutions of the two individual components (C7 or P9) showed increased thermal displacement at longer time scales. This positive slope in MSD is indicative of freely flowing liquids. These results confirm the visual observation that solutions of C7 and P9 are freely flowing liquids when kept separate from one another (FIG. 6A). In contrast, fluorosphere displacement was found to be independent of time once the two components were mixed together, indicative of formation of a hydrogel network. As the weight percent of the solution was increased from 5 to 10%, the onset of gelation was significantly faster (data not shown, all gels formed within ~10 seconds) and the resulting hydrogels demonstrated greater bead confinement, consistent with stiffer gels (FIG. 6B). The ideal viscoelastic properties of hydrogels for cell transplantation applications are not yet well understood; however the gel should result in uniform cell suspensions and the properties may need to be optimized for specific cell types. It is now well documented that cell morphology, adhesion, differentiation, and gene expression are altered in response to biomechanical cues. Therefore, the ability to systematically tune the hydrogel viscoelastic properties is critical. Our modular design strategy would allow systematic control over the hydrogel viscoelasticity through selection and molecular-level arrangement of the individual association domains. As demonstrated, by substituting the C7 component with the weaker binding N7 component, the resulting hydrogels were significantly more compliant (FIGS. 6B-C). Therefore, a higher weight percent of N7:P9 (>8%) is required to form a gel compared to C7:P9 (5%) (FIGS. 6B-C). These results demonstrate that judicious selection of the molecular-level peptide building blocks can be used to predictably tune the macroscopic hydrogel viscoelastic properties.

Figure 7A:
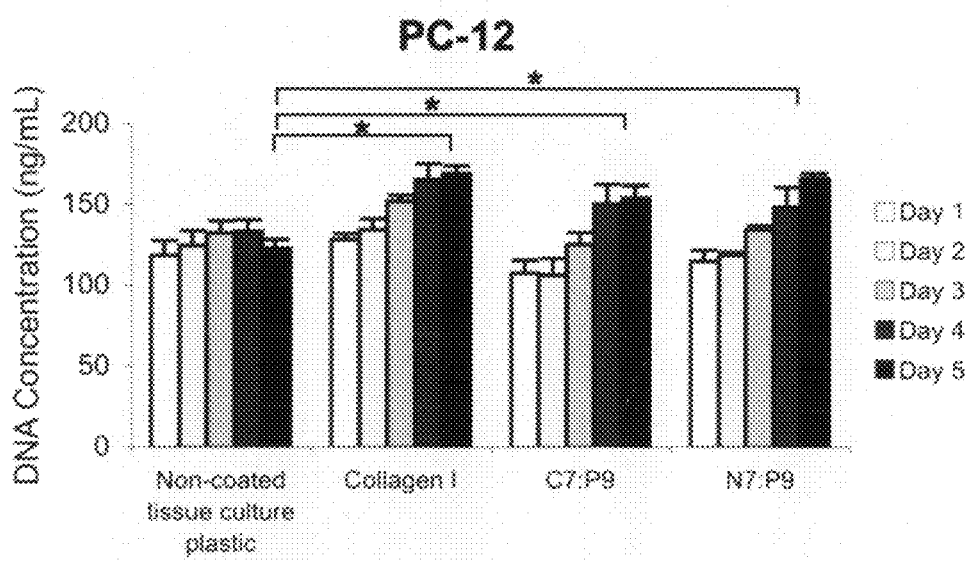
FIGS. 7A-B shows examples of PC-12 and adult NPC viability and differentiation on 2D films according to an embodiment of the invention.
Figure 7B:
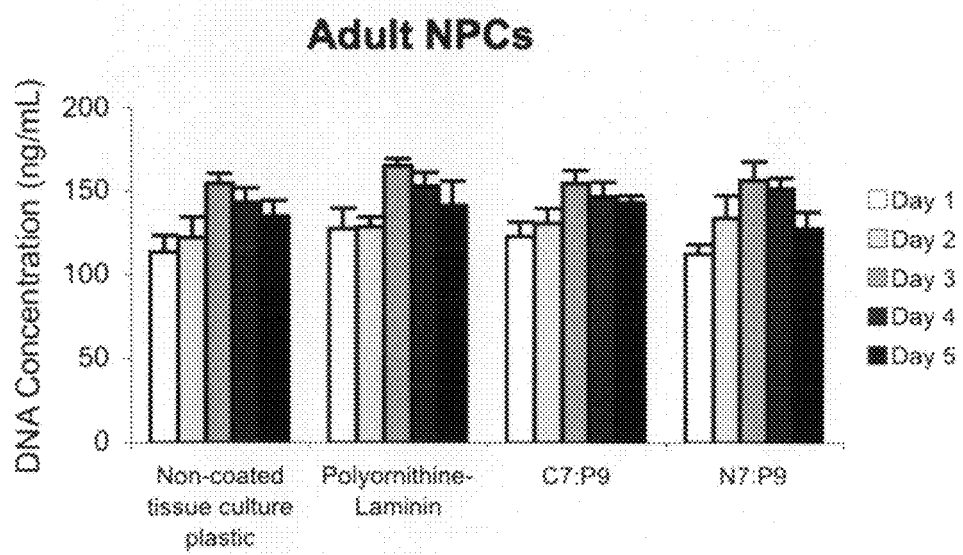

The bioactivity and biocompatibility of the physical hydrogels were initially assessed on 2D films of the C7:P9 and N7:P9 hydrogels using a neuronal-like PC-12 cell line and adult murine neural progenitor cells (NPC). Making use of the precision of protein engineering, we incorporated biofunctionality into the hydrogels by introducing a fibronectin-derived RGDS cell-adhesion sequence within hydrophilic spacer 1 (FIG. 2). PC-12 cell proliferation on C7:P9 and N7:P9 films, as monitored by DNA quantification, was found to be comparable to that on a positive control collagen I substrate and enhanced over non-coated tissue culture plastic, a common negative control material for adherent PC-12 cells (FIGS. 7A-B). For NPCs, which do not require substrate adhesion for viability, DNA quantification on all substrates was similar (FIGS. 7A-B). Additionally, NPCs grown on C7:P9 and N7:P9 hydrogel films were able to maintain their neural multipotency as observed via nestin-positive immunocytochemistry when cultured in proliferation medium. Cultures of both PC-12 and NPCs on C7:P9 and N7:P9 hydrogel films adopted typical neural morphologies after differentiation, with PC-12 cells showing long neuronal extensions and NPCs displaying glial (GFAP-positive) and neuronal (MAP2-positive) phenotypes.

Figure 8A:
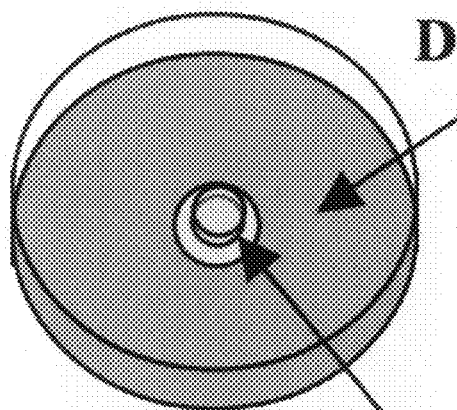
FIG. 8A-B show examples of a 3D cell encapsulation of adult NPC within hydrogel according of an embodiment of the invention (Schematic in FIG. 8A and Cell Image in FIG. 8B). 3D encapsulation of dissociated adult NPC was achieved by first mixing the cells (5×10$^6$ cells/ml) with the 10 μl solutions of 5% w/v C7 or N7 component before adding 10 μl of 5% w/v P9 component within a Teflon mold (Rainin Instrument, Oakland, Calif.) glued to the cover slip glass bottom of a 60-mm tissue culture plate (In Vitro Scientific, Sunnyvale, Calif.). The plate was then filled with either growth media or differentiation media.
Figure 8B:
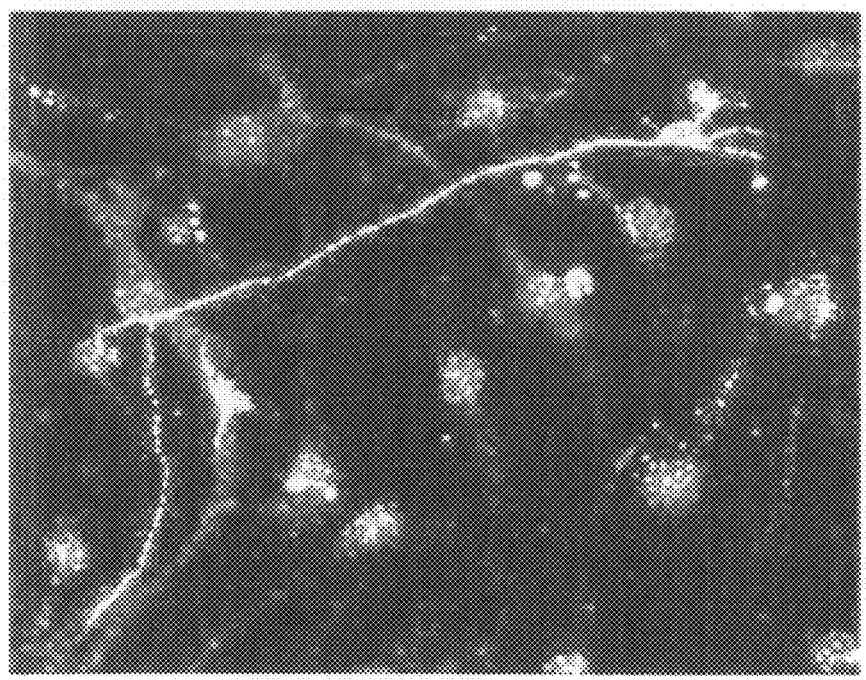

The two-component physical hydrogels presents the ability to encapsulate cells in 3D at constant physiological conditions. To demonstrate this, in one example, PC-12 and NPCs were pre-mixed with solutions of C7 or N7 prior to the addition of P9 to induce gelation (FIG. 8A-B). Confocal imaging of LIVE/DEAD stained samples showed high cell viability and uniform cell distribution five days after encapsulation, confirming the cytocompatibility of the encapsulation method of this invention and the lack of cytotoxicity of these physical hydrogels. Furthermore, the gelation mechanism based on specific molecular-recognition interactions for 3D encapsulation of cells, was unaffected by the presence of serum and other proteins such as growth factors, indicating that the other components present in the mixture did not interfere in the gelation process of our two-component system. This uniform cell distribution further confirms the fast gelation kinetics of our hydrogels, which form during mixing (<10 sec). These results are consistent with previous peptide assembly studies that reported decreasing the gelation time from 1 hour to 40 seconds resulted in homogeneous distributions of cells. Immunostaining of the 3D cultures of adult NPCs differentiated within C7:P9 and N7:P9 gels showed NPC differentiation into both neuronal and glial phenotypes, demonstrating that NPCs maintain their neural multipotency upon encapsulation and that scaffolds can support cell spreading, neurite outgrowth, and neurite branching.

These results clearly demonstrate a new strategy to easily encapsulate cells within injectable physical hydrogels. Gelation is based solely on the cumulative effects of specific molecular-recognition interactions between WW domains and polyproline-rich peptides repeated within the sequences of two distinct engineered components. The design of the individual components with spacers connecting multiple association domains was not observed to negatively affect the folding of the WW domains into the triple-stranded β-sheet conformation essential for interactions with polyproline-rich peptides. Through engineering of the molecular-level design, the number of repeating domains per chain and the dissociation constant between the two components were precisely altered. These design parameters at the molecular-level provide direct control of the macroscopic hydrogel viscoelastic properties. The two-component gelation strategy allows simple and gentle 3D cell encapsulation without compromising cell viability and without the use of any environmental triggers. In addition, the fast gelation kinetics observed allows for uniform cell distribution and makes our hydrogel an attractive candidate for cell transplantation in vivo. The hydrogel material was shown to be non-cytotoxic and capable of promoting cell proliferation, differentiation, and neurite extension.

The adult central nervous system (CNS), unlike many other tissues, has a limited capacity for self-repair, and endogenous neural stem cells are restricted in their ability to generate new functional neurons in response to injury or disease. A promising treatment for spinal cord injuries includes the transplantation of stem cell populations into the injured site to promote axonal and neural tissue regeneration. Both adult neural progenitor and embryonic stem cells have produced partial functional recovery in animal models with a wide spectrum of lesions, varying in severity and level of injury. However, cells are mostly injected in medium alone during transplantation and often result in low viability following implantation, e.g., up to 85% of the cells die during or shortly after the implantation procedure, and trial outcomes are often unpredictable. Cell viability is thought to be a critical component of successful cell transplantation therapy and has been shown to directly correlate to functional outcome. Therefore, there is a strong need to develop new efficient methods of delivery of transplanted cells to the lesioned or diseased tissue of the central nervous system. We argue that this two-component system may substantially enhance neuronal cell survival during direct cell injection.

The precision of protein engineering allows both components to be easily modified to incorporate other selective cell-binding domains into the hydrophilic spacers to target the growth of specific cell types as well as the release of specific growth factors and is currently under way. This biosynthetic strategy further enables exact molecular-level design of the repeating polymers, which will provide insights into the relationship between network structure and macroscopic hydrogel properties. This new approach to forming a physical hydrogel that facilitates cell encapsulation under normal physiological conditions without the use of external environmental triggers will enhance cell viability, be easily transferred to surgical procedures, and contribute to the success of cell transplantation therapies.

Materials and Methods

Protein Engineering

WW domain block copolymers (N3-7 and C3-7) and polyproline peptide chains (P3-9) were cloned into the pET-15b vector (Novagen, San Diego, Calif.), expressed in BL21 (DE3) *Escherichia coli* host strain (Novagen), and purified via specific binding of an N-terminal His-Tag sequence to Ni-NTA resin (Qiagen, Valencia, Calif.).

Binding Assays

Tryptophan fluorescence-based peptide binding assays were conducted on a SpectraMax Gemini EM spectrofluorometer (Molecular Devices, Sunnyvale, Calif.), monitoring the intrinsic fluorescence emission of the tryptophan residues at 340 nm (excitation at 295 nm). Binding assays for 1 μM C3 and N3 were conducted in triplicate at 25° C. in buffer TN (100 mM TrisHCL, 100 mM NaCl, pH 8.0) with $10^{-9}$ to $10^{-3}$ M P3.

Isothermal titration calorimetry measurements were made using a MicroCal VP-ITC microcalorimeter (Microcal, Inc., Northhampton, Mass.) in buffer TN at 25° C., starting with 150 μM C3 or N3 recombinant proteins in the sample cell and titrating 1.5 to 2.2 mM P3, sixty-three injections. Data were fitted using a one-site binding model with MicroCal Origin software.

Particle Tracking

Microrheology particle tracking experiments were performed using 0.2 micron-sized tracer fluorescent particles (Molecular Probes, Carlsbad, Calif.) added to 10 μl solutions of 10 to 5% w/v C7, 10 to 5% w/v N7, and 10 to 5% w/v P9 in buffer TN. 10 μl samples were pipetted between a microscope slide and a cover slip separated by a 120 μm thick SecureSeal Imaging Spacer (Grace Biolabs, Bend, Oreg.). Particle tracking was conducted using a Zeiss microscope equipped with an ANDOR iXON DV897 camera (ANDOR Technology, South Windsor, Conn.).

The Brownian dynamics of 20-50 embedded beads were followed simultaneously under a 40× oil objective with a temporal resolution of ~30 Hz for ~15 seconds. Stacks of tiff images were analyzed following the methods and macros developed by Crocker and Grier (27) (1996) using IDL software version 7.0.

Cell Culture and Differentiation

PC-12 cells were cultured on BD Primaria tissue culture plastic dishes using F-12 Kaighn's modified media with L-glutamine, containing 10% heat-inactivated horse serum, 5% fetal bovine serum, and 100 U/ml, 100 μg/ml penicillin-streptomycin (P/S) solution. For differentiation, cells were seeded at a density of $1 \times 10^4$ cells/cm$^2$ and primed for 1 day in PC-12 culture media before differentiating for 7 days in F-12K media containing 100 U/ml, 100 μg/ml P/S solution and 50 ng/ml recombinant human beta nerve growth factor (R&D Systems, Minneapolis, Minn.).

Murine adult neural progenitor cells (NPC) were isolated as previously described and cultured as neurospheres in tissue culture plastic flasks using Neurobasal—A media supplemented with 1% glutamax, 2% B27 vitamin, 20 ng/ml epidermal growth factor (EGF) and 20 ng/ml fibroblast growth factor (FGF). For differentiation, cells were seeded at a density of $1 \times 10^4$ cells/cm$^2$ and primed for 1 day in adult NPC growth media before changing to differentiation medium (low FGF concentration—5 ng/ml) for 2 days and finally, replacing with Neurobasal—A media supplemented with 1% glutamax and 2% B27 vitamin only for 3 days. Adult NPC were cultured as a single cell monolayer in polyomithine-laminin coated tissue culture plastic flasks.

Cell Proliferation Assay

PC-12 and adult NPC cell proliferation on various substrates (tissue culture plastic, collagen I, polyornithine-laminin, C7:P9 films, and N7:P9 films) was assessed by total DNA quantification using the PicoGreen assay (Molecular Probes, Carlsbad, Calif.). Cells were seeded in quadruplicate at $1 \times 10^4$ cells/cm$^2$ on the different substrates cast into the wells of 24-well plates and incubated at 37° C. and 5% $CO_2$. After 1 to 5 days, the media in each well was removed and the cells disrupted by adding 1 ml of lysis buffer (0.2% Triton-X and 5 mM $MgCl_2$) to each well and incubating in the dark for 48 h. The lysates were centrifuged at 3000 g and RT for 10 min. The supernatant was mixed with diluted PicoGreen solution (PicoGreen dimethylsulfoxide stock solution diluted 200× in TE assay buffer) according to the manufacturer's protocol. After thorough mixing, 100 μl of the solution was transferred to a 96-well assay plate and fluorescence measurements were taken at $\lambda_{ex}$ and $\lambda_{em}$ of 480 and 528 nm, respectively, using a SpectraMax M2 Spectrophotometer (Molecular Devices, Sunnyvale, Calif.). Statistical analysis was performed using SPSS Statistics v16.0 software (Chicago, Ill.). One-way analysis of variance (ANOVA) was performed followed by Tukey post-test and statistically significant differences with $p<0.05$, $p<0.01$ and $p<0.001$ were noted (only statistically significant differences with $p<0.001$ are shown on the bar graphs).

Cell Encapsulation 3D encapsulation of PC-12, adult NPC neurospheres, and dissociated adult NPC was achieved by first mixing the cells ($5 \times 10^6$ cells/ml) with the 10 μl solutions of 5% w/v C7 or N7 component before adding 10 μl of 5% w/v P9 component within a Teflon mold (Rainin.

Instrument, Oakland, Calif.) glued to the cover slip glass bottom of a 60-mm tissue culture plate (In Vitro Scientific, Sunnyvale, Calif.). The plate was then filled with either growth media or differentiation media.

LIVE/DEAD Assay

Cell viability within hydrogels was assessed with a LIVE/DEAD kit, a fluorescence-based membrane integrity assay (Molecular Probes, Carlsbad, Calif.). PC-12 cells and mouse adult NPC neurospheres encapsulated within hydrogels, were cultured for 5 days in growth media before incubating in PBS containing 1.0 μM calcein-AM and 2.0 μM ethidium homodimer for 30 to 45 min and were directly visualized by laser confocal microscopy. All images were captured using a Leica Laser Scanning Microscope equipped with an Axiovert microscope, 40× oil immersion objective (Zeiss Achroplan 10, numerical aperture 0.3, working distance 3.1 mm).

Immunocytochemical Staining

Cultures were fixed in 4% paraformaldehyde in 0.1 M phosphate buffer (PBS, pH 7.4) for 15-30 minutes. After washes with PBS, cells were blocked with 10% normal goat serum (Invitrogen, Carlsbad, Calif.) containing 0.1% v/v Triton X-100 in phosphate-buffered saline (PBST). Primary antibodies were diluted in 0.1% PBST solution containing 5% normal goat serum and incubated overnight. After washes with 0.1% PBST, secondary antibodies were diluted in 0.1% PBST and the cells were incubated for 2 h at room temperature.

The following primary antibodies and dilutions were used: rabbit anti-neuronal class III (β-tubulin (TuJ1) 1:500 (Covance, Berkeley, Calif.); mouse anti-nestin 1:500 (BD Pharmingen, San Jose, Calif.); rabbit anti-microtubule-associated protein 2 (MAP2) 1:1000 (Chemicon, Temecula, Calif.); guinea pig anti-GFAP 1:300 (Advanced Immunochemicals, Long Beach, Calif.). Fluorescently coupled secondary antibodies were raised in goat (Alexafluor® 488, 546 and 633 and used at 1:500. DAPI was used as a nuclear counterstain (Roche, Indianapolis, Ind.). A Zeiss Axiovert 200M fluorescence microscope with a 40× oil objective (Carl Zeiss Microimaging, Thornwood, N.Y.) and a Leica TCS/SP2 confocal microscope (Leica, Bensheim) were used to evaluate fluorescent stainings.

What is claimed is:

1. A viscoelastic hydrogel, comprising: a first protein hetero-assembled with a second protein, wherein the first protein cannot self-assemble with itself, wherein the second protein cannot self-assemble with itself, wherein the first protein includes a first association sequence (1stA) and a first spacer (1stSp), wherein the second protein includes a second association sequence (2ndA) and a second spacer (2ndSp), wherein the first association sequence and the second association sequence interact with each other with a 1:1 stoichiometry to form a three dimensional scaffold, wherein the first protein is represented by $\{1stA(1stSp)\}_x 1stA$, where x is $\geq 2$, and the second protein is represented by $\{2ndA(2ndSp)\}_3 2ndA$, where y $\geq 2$.

2. The viscoelastic hydrogel as set forth in claim 1, wherein the first protein is represented by $\{1stA(1stSp)_m\}_x 1stA$, where m is 1 to 50, and x is 2 to 15; and the second protein is represented by $\{2ndA(2ndSp)\}_y 2ndA$, where n is 1 to 50, and y is 2 to 15, and wherein m and n are non-integer multiples of one another.

3. The viscoelastic hydrogel as set forth in claim 1, wherein the first association sequence is a WW protein sequence and the second protein is a polyproline-rich sequence.

4. The viscoelastic hydrogel as set forth in claim 1, wherein the first spacer is a first hydrophilic spacer protein sequence and the second spacer a second hydrophilic spacer protein sequence, wherein the first hydrophilic spacer protein sequence and the second hydrophilic spacer protein sequence are not the same.

5. The viscoelastic hydrogel as set forth in claim 1, wherein the first spacer is a first hydrophilic spacer protein sequence and the second spacer a second hydrophilic spacer protein sequence, wherein the first hydrophilic spacer protein sequence and the second hydrophilic spacer protein sequence differ in the number of repetitions of their respective sequences.

6. The viscoelastic hydrogel as set forth in claim 1, wherein the first spacer is a first hydrophilic spacer protein sequence and the second spacer a second hydrophilic spacer protein sequence, wherein the first hydrophilic spacer protein sequence and the second hydrophilic spacer protein sequence are based on the same protein sequences but differ in the number of repetitions of the protein sequences.

7. The viscoelastic hydrogel as set forth in claim 1, wherein the first spacer is a first hydrophilic spacer protein sequence and the second spacer a second hydrophilic spacer protein sequence, wherein the first hydrophilic spacer protein sequence is longer than the second hydrophilic spacer protein sequence.

* * * * *